(12) United States Patent
Smith

(10) Patent No.: US 7,741,469 B2
(45) Date of Patent: Jun. 22, 2010

(54) COMPOSITIONS FOR TREATING HEARING LOSS AND METHODS OF USE THEREOF

(75) Inventor: Richard J. Smith, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 0 days.

(21) Appl. No.: 11/732,619

(22) Filed: Apr. 4, 2007

(65) Prior Publication Data

US 2007/0243242 A1 Oct. 18, 2007

Related U.S. Application Data

(60) Provisional application No. 60/789,460, filed on Apr. 5, 2006.

(51) Int. Cl.
- A01N 43/04 (2006.01)
- A61K 31/70 (2006.01)
- C07H 21/02 (2006.01)
- C07H 21/04 (2006.01)
- C12Q 1/68 (2006.01)
- C12Q 19/34 (2006.01)

(52) U.S. Cl. ............ 536/24.5; 536/23.1; 536/24.3; 536/24.33; 514/44; 435/6; 435/91.1; 435/325; 435/375

(58) Field of Classification Search .......... 536/23.1, 536/24.3, 24.33, 24.5
See application file for complete search history.

(56) References Cited

U.S. PATENT DOCUMENTS 4,683,195 A 7/1987 Mullis et al.
4,683,202 A 7/1987 Mullis
4,800,159 A 1/1989 Mullis et al.
4,965,188 A 10/1990 Mullis et al.
5,624,803 A 4/1997 Noonberg et al.
6,395,713 B1 5/2002 Beigelman et al.
2005/0182007 A1* 8/2005 McSwiggen et al. .......... 514/44

FOREIGN PATENT DOCUMENTS

WO WO 93/23569 11/1993
WO WO 94/02595 2/1994
WO WO 96/10390 4/1996

(Continued)

OTHER PUBLICATIONS

Yano et al. Molecular Carcinogenesis, 2001 vol. 31:101-109.*

(Continued)

*Primary Examiner*—Sean McGarry
*Assistant Examiner*—Terra Cotta Gibbs
(74) *Attorney, Agent, or Firm*—Viksnins Harris & Padys PLLP

(57) ABSTRACT

This invention also relates to compounds, compositions, and methods useful for modulating the expression and activity of genes encoding proteins involved in deafness caused by dominant negative mechanism of action by RNA interference (RNAi) using small nucleic acid molecules. In particular, the instant invention features small nucleic acid molecules, such as short interfering nucleic acid, short interfering RNA, double-stranded RNA (dsRNA), micro-RNA (mRNA), and short hairpin RNA (shRNA) molecules and methods used to modulate the expression of genes involved in deafness caused by dominant negative mechanism of action.

16 Claims, 5 Drawing Sheets

FOREIGN PATENT DOCUMENTS

| | | |
|---|---|---|
| WO | WO 96/10391 | 4/1996 |
| WO | WO 96/10392 | 4/1996 |
| WO | WO 96/18736 | 6/1996 |

OTHER PUBLICATIONS

Hammond et al. Nature Reviews, 2001 vol. 2:110-119.*
Scanlon, KJ. Current Pharmaceutical Biotechnology, 2004 vol. 5:415-420.*
GenBank Accession No. AF281280, published Aug. 2, 2000.*
Ambion siRNA target finder (http://www.ambion.com/techlib/misc/siRNA_finder.html, available 2002 to the public, results for GenBank Accession No. AF281280).*
Internet Archive WayBackMachine (http://web.archive.org/web/*/http://www.ambion.com/techlib/misc/siRNA_finder.html).*
Aldrian-Herrada et al., 1998, Nucleic Acids Res., 26, 4910-4916.
Boado et al., 1998, J. Pharm. Sci., 87, 1308-1315.
Boado, 1995, Adv. Drug Delivery Rev., 15, 73-107.
Chen et al., 1992, Nucleic Acids Res., 20, 4581-9.
Chowrira et al., 1994, J. Biol. Chem., 269, 25856).
Coucke PJ, et al. Hum Mol Genet 1999; 8(7): 1321-8.
Couture et al., 1996, TIG., 12, 510.
Denoyelle, F. et al. *Hum. Mol. Genet.* 6, 2173-2177. (1997).
Denoyelle, F et al. *Nature.* 393, 319-320 (1998).
Di, W.L. et al., *Cell Commun. Adhes.* 8 415-418 (2001).
Dropulic et al., 1992, J. Virol., 66, 1432-41.
Duckert, L.G. et al.. *Otolaryngology*. 86, 434-446 (1978).
Elbashir, S.M. et al., *EMBO J.* 20, 6877-6888 (2001).
Elroy-Stein and Moss, 1990, Proc. Natl. Acad. Sci. USA, 87, 6743-7.
Emerich, DF et al, 1999, Cell Transplant, 8, 47-58.
Estivill, X. et al. *Lancet.* 351, 394-398 (1998).
Fire A. Trends Genet 1999; 15(9): 358-63.
Frier et al., 1986, Proc. Nat. Acad. Sci. USA 83:9373-9377.
Gao and Huang 1993, Nucleic Acids Res., 21, 2867-72.
Good et al., 1997, Gene Therapy, 4, 45.
Green, G.E. et al. *JAMA.* 281, 2211-2216 (1999).
Ishiwata et al., Chem. Pharm. Bull. 1995, 43, 1005-1011.
Izant and Weintraub, 1985, Science, 229, 345.
Janecke, A.R. et al. *Hum. Genet.* 108, 269-270 (2001).
Jero J, et al. Hum Gene Ther 2001; 12(5): 539-48).
Jolliet-Riant and Tillement, 1999, Fundam. Clin. Pharmacol., 13, 16-26.
Kashani-Sabet et al., 1992, Antisense Res. Dev., 2, 3-15.
Kelsell, D.P. et al. *Nature* 387, 80-83 (1997).
Kharkovets T, et al. EMBO J 2006; 25(3): 642-52. Epub Jan. 26, 2006.
Kubisch C, et al. Cell 1999; 96(3): 437-46.
Landegran et al., 1988, *Science*, 241:1077-1080.
Lasic et al., Science 1995, 267, 1275-1276.
Lasic et al. Chem. Rev. 1995, 95, 2601-2627.
Lee et al., 2002, *Nat. Biotech.*, 20:500-5.
Lieber et al., 1993, Methods Enzymol., 217, 47-66.
Liu et al., J. Biol. Chem. 1995, 42, 24864-24870.
Lisziewicz et al., 1993, Proc. Natl. Acad. Sci. U S. A, 90, 80004.
L'Huillier et al., 1992, EMBO J, 11, 4411-8.
Martinez, J. et al., *Cell* 110, 563-574 (2002).
Marziano, N.K. et al., *Hum. Mol. Genet.* 12, 805-812 (2003).
McGarry and Lindquist, 1986, Proc. Natl. Acad. Sci., USA 83, 399.
McGuirt, W.T. et al. *Nat. Genet.* 23, 413-419 (1999).
Miyagishi and Taira, 2002, Nature Biotechnology, 19, 497.
Nakazawa et al., 1994, *Proc. Natl. Acad. Sci. USA*, 91:360-364.
Noonberg et al., 1994, Nucleic Acid Res., 22, 2830.
Ohkawa et al., 1992, Nucleic Acids Symp. Ser., 27, 15-6.
Oku et al., 1995, Biochim. Biophys. Acta, 1238, 86-90.
Ojwang et al., 1992, Proc. Natl. Acad. Sci. USA, 89, 10802-6.
Pardridge et al., 1995, PNAS USA., 92, 5592-5596.
Paul et al., 2002, Nature Biotechnology, 19, 505.
Prieskorn, D.M. & Miller, J.M. *Hear. Res.* 140, 212-215 (2000).
Richard, G. et al. *Hum. Genet.* 103, 393-399 (1998).
Rouan, F. et al., *J. Cell Sci.* 114, 2105-2113 (2001).
Sarver et al., 1990 Science, 247, 1222-1225.
Scanlon et al., 1991, Proc. Natl. Acad. Sci. USA, 88, 10591-5.
Schroeder et al., Prog Neuropsychopharmacol Biol Psychiatry, 23, 941-949, 1999.
Shepherd, R.K. et al., *Arch. Otolaryngol. Head Neck Surg.* 130, 518-523 (2004).
Sullenger & Cech, 1993, Science, 262, 1566.
Taira et al., 1991, Nucleic Acids Res., 19, 5125-30.
Templeton, N.S. et al. *Nat. Biotechnol.* 15, 647-652 (1997).
Thompson et al., 1995, Nucleic Acids Res., 23, 2259.
Turner et al., 1987, CSH Symp. Quant. Biol. LII pp. 123-133.
Turner et al., 1987, J. Am. Chem. Soc. 109:3783-3785.
Tyler et al., 1999, PNAS USA., 96, 7053-7058.
Tyler et al., 1999, FEBS Lett., 421, 280-284.
van Hauwe P, et al. Am J Med Genet 2000; 93(3): 184-7.
Ventura et al., 1993, Nucleic Acids Res., 21, 3249-55.
Wadhwa, R. et al., *Mutat. Res.* 567, 71-84 (2004).
Weerasinghe et al., 1991, J. Virol., 65, 55314.
Yu et al., 1993, Proc. Natl. Acad. Sci. USA, 90, 6340-4.
Zhou et al., 1990, Mol. Cell. Biol., 10, 4529-37.
Applied Biosystems TechNotes 10(4), Sep. 2003.
Elbashir et al., (2001) Nature 411:494-498.
Harborth et al., (2003) Antisense Nucleic Acid Drug Dev. 13:83-106.
Tuschl lab (May 8, 2003) "The siRNA user guide".
Semizarov et al., (2003) Proc. Natl Acad Sci USA 100:6347-6352.
Jackson et al., (2003) Nat Biotechnol. 21:635-637.
Editors of Nature Cell Biology, (2003) Nat. Cell. Bio. 5:489-490.
Screen-shot, siRNA Target Finder, 2008.
Reynolds et al., (2004) Nat Biotechnol. 22(3):326-30.

* cited by examiner (*P<0.05; n=7, Bars; Mean±SD)

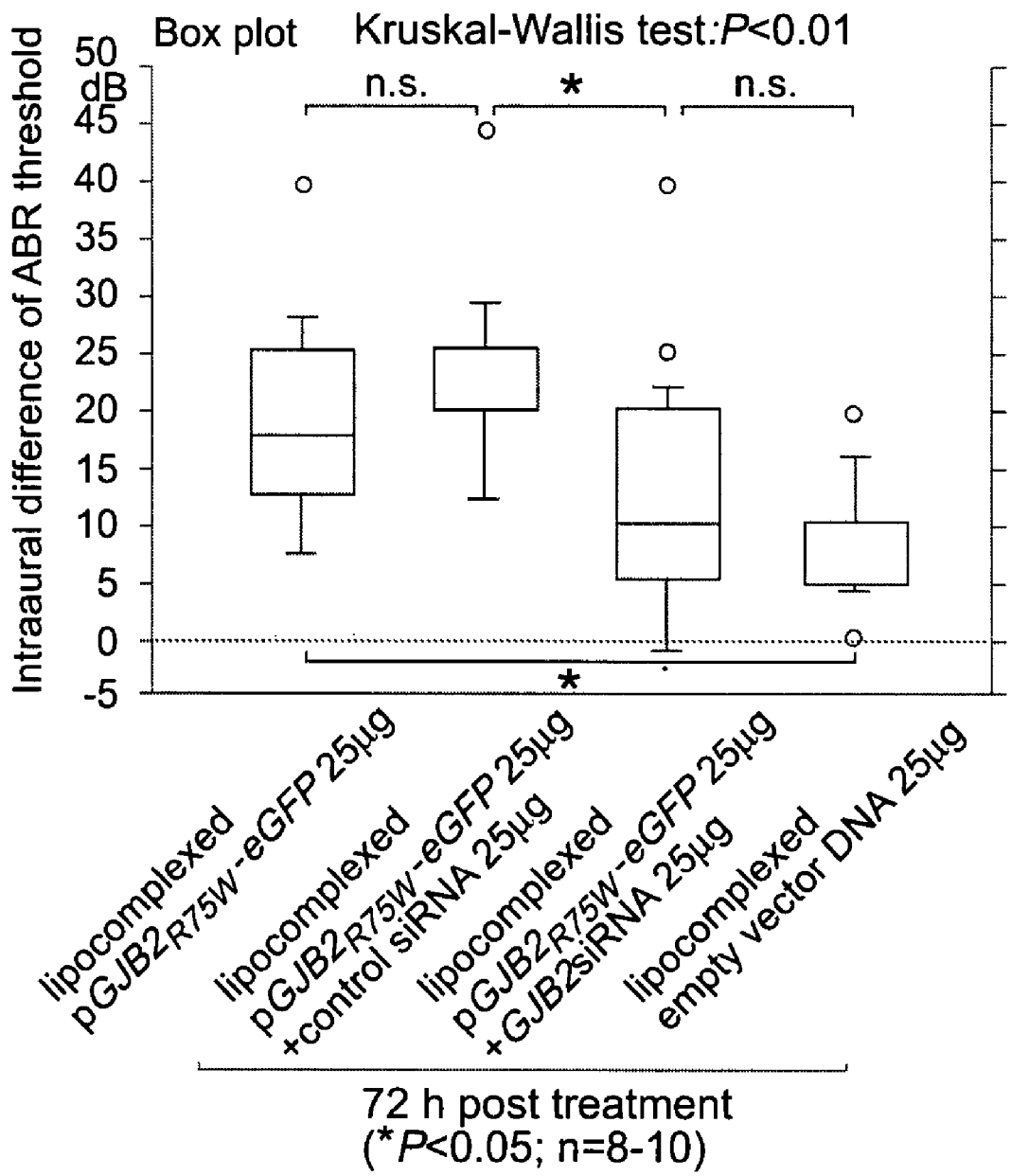

US 7,741,469 B2

COMPOSITIONS FOR TREATING HEARING LOSS AND METHODS OF USE THEREOF

RELATED APPLICATION

This patent document claims the benefit of priority of U.S. Application Ser. No. 60/789,460, filed Apr. 5, 2006, which application is herein incorporated by reference.

STATEMENT REGARDING GOVERNMENT FUNDING

This research was supported in part by NIH grant DC03544. The U.S. government has certain rights in the invention.

FIELD OF THE INVENTION

The present invention is directed to compounds, compositions, and methods relating to traits, diseases and conditions that respond to the modulation of expression and/or activity of genes encoding proteins involved in deafness caused by dominant negative mechanism of action. Specifically, the invention relates to small nucleic acid molecules, such as short interfering nucleic acid, short interfering RNA (siRNA), double-stranded RNA (dsRNA), micro-RNA (mRNA), and short hairpin RNA (shRNA) molecules capable of mediating RNA interference (RNAi) against gene expression. Such small nucleic acid molecules are useful, for example, in providing compositions and methods for treating hearing loss.

BACKGROUND OF THE INVENTION

RNA interference (RNAi) is a post-transcriptional process in which double stranded RNA (dsRNA) triggers sequence-specific suppression of homologous genes. The first evidence that dsRNA leads to post-transcriptional gene silencing in animals came from work on *Caenorhabditis elegans*. As reconstructed in cell extract experiments in *Drosophila melanogaster* and *Homo sapiens*, dsRNA is digested into 21-23 nucleotide (nt) fragments of small interfering RNA (siRNA) by a member of the RNase III family of ATP-dependent, dsRNA-specific ribonucleases called Dicer.

These siRNA duplexes bind to a nuclease complex to form the RNA-induced silencing complex (RISC), with the antisense strand serving as a cognate template for specific transcript recognition. RISC catalyzes cleavage of specific mRNAs, which is followed by rapid degradation by cellular exonuclease activity. Longer dsRNAs (>50 bp) have a more widespread effect in mammalian somatic cells, inducing general arrest of protein synthesis through an interferon response and protein kinase activation. Shorter siRNAs of 21-23 nt, in contrast, have a more targeted effect, inducing up to 90% depletion of specific mRNAs both in vitro and in vivo.

The ear is exquisitely sensitive, being able to detect frequencies from as low as 16 Hz to as high as 20,000 Hz. This incredible sensitivity is based in the membranous labyrinth housed in the bony cochlea, a spiral canal about 31-33 mm long winding 2½ times around a central bony modiolus. The pars inferior of the membranous labyrinth includes the human cochlea, which has 3500 inner hair cells and about 12,000 outer hair cells. The hair cells have stereocilia, about 120 stereocilia on each inner hair cell and 46-148 stereocilia on each outer hair cell.

The most obvious abnormality of inner ear function is deafness, the most common of sensory deficits. Congenital deafness, for example, affects approximately one in 1,000 children. In half of these newborns, the cause is environmental, and in half, it is genetic. With age, the burden of genetic deafness increases to such an extent that by the age of 80, 50% of the population will have hearing loss sufficient in degree to require the use of amplification. The causes of this age-related hearing loss are complex and include both genetic and environmental factors.

Over the past decade, the scientific understanding of non-syndromic hereditary hearing loss has increased. Loci associated with autosomal dominant, autosomal recessive, x-linked, mitochondrial, and even modifier genes have been identified. Each locus is named with an appropriate prefix, for example DFNA for dominant and DFNB for recessive, followed by a suffix integer to indicate locus in order of discovery.

For many of these loci, the causally related genes have been cloned, and this knowledge has translated to clinical medicine and changed the way children and adults with presumed hereditary hearing loss are evaluated. There has been a dramatic increase in the number of requests from clinical diagnostic laboratories for genetic testing for hearing loss.

SUMMARY OF THE INVENTION

This invention relates to compounds, compositions, and methods useful for modulating the expression and activity of genes involved in deafness caused by dominant negative mechanism of action by RNA interference (RNAi) using small nucleic acid molecules. In particular, the instant invention features small nucleic acid molecules, such as short interfering nucleic acid, short interfering RNA, double-stranded RNA (dsRNA), micro-RNA (mRNA), and short hairpin RNA (shRNA) molecules and methods used to modulate the expression of genes encoding proteins involved in deafness caused by dominant negative mechanism of action. A nucleic acid molecule of the invention can be unmodified or chemically-modified. A nucleic acid molecule of the instant invention can be chemically synthesized, expressed from a vector or enzymatically synthesized.

In one embodiment, the invention features one or more nucleic acid molecules and methods that independently or in combination modulate the expression of genes encoding proteins involved in deafness caused by dominant negative mechanism of action. In certain embodiments, the present invention provides a composition that is an isolated nucleic acid molecule having a first portion, where in the first portion is no more than 30 nucleotides in length, where in the first portion is complementary to specific regions of mutations in genes known to cause autosomal dominant hearing loss through a dominant negative mechanism of action, wherein an example is specific mutations in Gap Junction Beta-2 (GJB2) protein.

In certain embodiment of the invention, siRNAs are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when siRNA initiates the degradation of the mRNA transcribed from a gene of interest in a sequence-specific manner via RNA interference, thereby preventing translation of the gene's product.

In certain embodiments, the present invention provides a composition that is an isolated nucleic acid molecule (e.g., RNA) having a first portion, wherein the first portion is comprises a sequence that is complementary to target sequence 5'-AAC GTG TGC TAC GAT CAC TAC-3' (siRNA1; SEQ ID NO:1), 5'-AAG TTC ATC AAG GGG GAG ATA-3' (siRNA2; SEQ ID NO:3), or 5'-AAG ACT GTC TTC ACA GTG TTC-3' (siRNA3; SEQ ID NO:5). In certain embodiments, the composition further contains a second portion, wherein the second portion has a sequence that is substantially complementary to the first portion. As used herein, the term "substantially complementary to" means that the two strands are at least 50%, 55%, 60%, 70%, 75%, 76%, 77%, 78%, 79%, 80%, 81%, 82%, 83%, 84%, 84%, 85%, 86%, 87%, 88%, 89%, 90%, 91%, 92%, 93%, 94%, 95%, 96%, 97%, 98%, 99%, or 100% complementary to each other. As used herein the term "encoded by" is used in a broad sense. For example, the statement "the first portion of RNA is encoded by SEQ ID NO:1" means that a first portion of RNA sequence corresponds to the RNA sequence transcribed from the DNA sequence indicated in SEQ ID NO:1, but may also contain additional nucleotides at either the 3' end or at the 5' end of the RNA molecule.

In certain embodiments, the first portion is operably linked to the second portion via a linker molecule. In certain embodiments the linker molecule is a polynucleotide linker, and in other embodiments, the linker molecule is a non-nucleotide linker. The linker molecule may form a loop of a hairpin. In certain embodiments, the linker molecule is about 4 to about 10 nucleotides in length. In certain embodiments, the first portion is from about 19 to about 23 nucleotides in length (e.g., is about 21 nucleotides). In certain embodiments, about 19 nucleotides of the first portion is base-paired to the complementary nucleotides of the second portion and wherein at least two 3' terminal nucleotides of first and second portions are not base-paired to the nucleotides of the other portion. In certain embodiments, all of the about 21 nucleotides of the first portion are base-paired to the complementary nucleotides of the second portion.

The present invention also provides a vector comprising an isolated nucleic acid molecule having a first portion, wherein the first portion is no more than 30 nucleotides in length, wherein the first portion is complementary to target sequence siRNA1, siRNA2, or siRNA3, and host cells containing such a vector.

The present invention provides a pharmaceutical composition comprising an isolated nucleic acid molecule having a first portion, wherein the first portion is no more than 30 nucleotides in length, wherein the first portion is complementary to siRNA1, siRNA2, or siRNA3, or a vector containing an isolated nucleic acid molecule having a first portion, wherein the first portion is no more than 30 nucleotides in length, wherein the first portion is complementary to siRNA1, siRNA2, or siRNA3. The pharmaceutical compositions of the present invention may be contained in a liposome. The pharmaceutical compositions of the present invention may further contain a pharmaceutically acceptable carrier or diluent.

The present invention provides a method of reducing the expression of GJB2 in a cell, by introducing an isolated nucleic acid molecule, vector, or pharmaceutical composition complementary to siRNA1, siRNA2, or siRNA3, into the cell in an amount sufficient to modulate the expression of GJB2 in the cell. In certain embodiments, the expression of GJB2 is reduced by at least 10%, 20%, 30%, 40%, 50%, 60%, 70%, 80%, 90% 95% or 100%. In certain embodiments, the cells in which expression is reduced are supporting cells in the inner ear. In certain embodiments, the cells in which expression is reduced are inner and/or outer hair cells of the inner ear. In certain embodiments, the cells in which expression is reduced are cells of the stria vascularis of the inner ear. In certain embodiments, the cells in which expression is reduced are fibrocytes of the inner ear. The cells to be targeted for reduction of gene expression are determined by the normal expression profile of those cells and the type of dominant negative deafness to be treated. In certain embodiments, the cell is in vivo. In certain embodiments, the cell is in a mammal, such as a human.

The present invention provides methods of reducing expression of genes that cause dominant negative hearing loss in cells in the inner ear by directly contacting the round window membrane with an isolated nucleic acid molecule, vector, or the pharmacological composition described above in an amount sufficient to reduce expression of the desired gene in the cell. In one embodiment, the present invention provides methods of reducing the expression of GJB2 in a cell, by directly contacting a round window membrane with an isolated nucleic acid molecule, vector, or the pharmaceutical composition described above in an amount sufficient to reduce the expression of GJB2 in the cell.

The present invention provides an isolated double stranded Gap Junction Beta-2 (GJB2) RNA molecule, wherein each strand of the RNA molecule is less than 30 nucleotides in length, and wherein one strand of the RNA molecule comprises nucleotide sequence substantially complementary to GJB2 so that the RNA molecule modulate expression of GJB2 via RNA interference.

In one embodiment, nucleic acid (NA) molecules of the invention are used to down regulate or inhibit the expression of genes encoding proteins involved in deafness caused by dominant negative mechanism of action. Analysis of the target gene (or protein or RNA levels associated with this gene) can be used to identify subjects with such polymorphisms or those subjects who are at risk of developing traits, conditions, or diseases described herein. These subjects are amenable to treatment, for example, treatment with NA molecules of the invention and any other composition useful in treating these diseases. As such, analysis of the target protein or RNA levels can be used to determine treatment type and the course of therapy in treating a subject.

In one embodiment of the invention a NA molecule comprises an antisense strand comprising a nucleotide sequence that is complementary to a nucleotide sequence or a portion thereof encoding a target protein. The NA further comprises a sense strand, wherein said sense strand comprises a nucleotide sequence of a target gene or a portion thereof.

In one embodiment of the invention a NA molecule (the "first portion") comprises an antisense strand having about 19 to about 29 (e.g., about 19, 20, 21, 22, 23, 24, 25, 26, 27, 28, or 29) nucleotides, wherein the antisense strand is complementary to the target gene, and wherein the NA further comprises a sense strand (the "second portion") having about 19 to about 29 (e.g., about 19, 20, 21, 22, 23, 24, 25, 26, 27, 28, or 29) nucleotides, and wherein the sense strand and the antisense strand are distinct nucleotide sequences with at least about 19 complementary nucleotides. Alternatively, the first portion and the second portion comprise a linear molecule with at least about 19 complementary nucleotides.

In one embodiment, nucleic acid molecules of the invention that act as mediators of the RNA interference gene silencing response are double-stranded nucleic acid molecules. In another embodiment, the NA molecules of the invention consist of duplex nucleic acid molecules containing about 19 base pairs between oligonucleotides comprising about 19 to about 25 (e.g., about 19, 20, 21, 22, 23, 24, or 25) nucleotides.

In yet another embodiment, nucleic acid molecules of the invention comprise duplex nucleic acid molecules with overhanging ends of about 1 to about 3 (e.g., about 1, 2, or 3) nucleotides, for example, about 21-nucleotide duplexes with about 19 base pairs and 3'-terminal mononucleotide, dinucleotide, or trinucleotide overhangs.

In another embodiment, the invention features a double-stranded short interfering nucleic acid molecule that down-regulates expression of a target gene encoding a protein involved in deafness caused by dominant negative mechanism of action, where the NA molecule contains an antisense region, wherein the antisense region comprises a nucleotide sequence that is complementary to a nucleotide sequence of the target gene or a portion thereof, and a sense region, wherein the sense region comprises a nucleotide sequence substantially similar to the nucleotide sequence of the target gene or a portion thereof. In one embodiment, the antisense region and the sense region each comprise about 19 to about 23 (e.g., about 19, 20, 21, 22, or 23) nucleotides, wherein the antisense region comprises about 19 nucleotides that are complementary to nucleotides of the sense region.

In another embodiment, the invention features a double-stranded short interfering nucleic acid molecule that down-regulates expression of a target gene encoding a protein involved in deafness caused by dominant negative mechanism of action comprising a sense region and an antisense region, wherein the antisense region comprises a nucleotide sequence that is complementary to a nucleotide sequence of RNA encoded by the target gene or a portion thereof and the sense region comprises a nucleotide sequence that is complementary to the antisense region.

In one embodiment, the invention features a double-stranded short interfering nucleic acid molecule that down-regulates expression of a target gene encoding a protein involved in deafness caused by dominant negative mechanism of action, wherein the NA molecule is assembled from two separate oligonucleotide fragments wherein one fragment comprises the sense region and the second fragment comprises the antisense region of the NA molecule. The sense region can be connected to the antisense region via a linker molecule, such as a polynucleotide linker or a non-nucleotide linker.

In one embodiment, the antisense region of a NA molecule of the invention comprises sequence complementary to a portion of a transcript having sequence unique to a particular disease, trait, or condition-related allele, such as sequence comprising a single nucleotide polymorphism (SNP) associated with the disease, trait, or condition specific allele. As such, the antisense region of a NA molecule of the invention can comprise sequence complementary to sequences that are unique to a particular allele to provide specificity in mediating selective RNAi against the disease, condition, or trait related allele.

In one embodiment, the invention features a medicament comprising a NA molecule of the invention.

In one embodiment, the invention features an active ingredient comprising a NA molecule of the invention.

One embodiment of the invention provides an expression vector comprising a nucleic acid sequence encoding at least one NA molecule of the invention in a manner that allows expression of the nucleic acid molecule. Another embodiment of the invention provides a mammalian cell comprising such an expression vector. The mammalian cell can be a human cell. The NA molecule of the expression vector can comprise a sense region and an antisense region. The antisense region can comprise sequence complementary to a RNA or DNA sequence encoding a target gene and the sense region can comprise sequence complementary to the antisense region. The NA molecule can comprise two distinct strands having complementary sense and antisense regions. The NA molecule can comprise a single strand having complementary sense and antisense regions.

In one embodiment, the invention features a method for modulating the expression of a target gene within a cell by introducing a NA molecule into a cell under conditions suitable to modulate the expression of a target gene in the cell.

In one embodiment, the invention features a method of modulating the expression of a target gene in an organism by introducing the NA molecule into the organism under conditions suitable to modulate the expression of the target gene in the organism. The level of target protein or RNA can be determined as is known in the art.

In one embodiment, the invention features a method for preventing or reducing deafness in an organism comprising contacting the organism with a NA molecule of the invention under conditions suitable to modulate the expression of the target gene in the organism.

The NA molecules of the invention can be designed to down regulate or inhibit target gene expression through RNAi targeting of a variety of RNA molecules. In one embodiment, the NA molecules of the invention are used to target various RNAs corresponding to a target gene. Non-limiting examples of such RNAs include messenger RNA (mRNA), alternate RNA splice variants of target gene(s), post-transcriptionally modified RNA of target gene(s), pre-mRNA of target gene(s), and/or RNA templates. If alternate splicing produces a family of transcripts that are distinguished by usage of appropriate exons, the instant invention can be used to modulate gene expression through the appropriate exons to specifically inhibit or to distinguish among the functions of gene family members. For example, a protein that contains an alternatively spliced transmembrane domain can be expressed in both membrane bound and secreted forms. Use of the invention to target the exon containing the transmembrane domain can be used to determine the functional consequences of pharmaceutical targeting of membrane bound as opposed to the secreted form of the protein. Non-limiting examples of applications of the invention relating to targeting these RNA molecules include therapeutic pharmaceutical applications, pharmaceutical discovery applications, molecular diagnostic and gene function applications, and gene mapping, for example using single nucleotide polymorphism mapping with NA molecules of the invention. Such applications can be implemented using known gene sequences or from partial sequences available from an expressed sequence tag (EST).

By "target site" is meant a sequence within a target RNA that is "targeted" for cleavage mediated by a NA construct which contains sequences within its antisense region that are complementary to the target sequence.

By "detectable level of cleavage" is meant cleavage of target RNA (and formation of cleaved product RNAs) to an extent sufficient to discern cleavage products above the background of RNAs produced by random degradation of the target RNA. Production of cleavage products from 1-5% of the target RNA is sufficient to detect above the background for most methods of detection.

By "phenotypic change" is meant any detectable change to a cell that occurs in response to contact or treatment with a nucleic acid molecule of the invention (e.g., NA). Such detectable changes include, but are not limited to, changes in shape, size, proliferation, motility, protein expression or RNA expression or other physical or chemical changes as can be assayed by methods known in the art. The detectable change can also include expression of reporter genes/molecules such as Green Florescent Protein (GFP) or various tags that are used to identify an expressed protein or any other cellular component that can be assayed.

In one embodiment, the invention features a kit containing a NA molecule of the invention that can be used to modulate the expression of a target gene in a biological system, including, for example, in a cell, tissue, or organism. In another embodiment, the invention features a kit containing more than one NA molecule of the invention that can be used to modulate the expression of more than one target gene in a biological system, including, for example, in a cell, tissue, or organism.

The present invention can be used alone or as a component of a kit having at least one of the reagents necessary to carry out the in vitro or in vivo introduction of RNA to test samples and/or subjects. For example, components of the kit include a NA molecule of the invention and a vehicle that promotes introduction of the NA into cells of interest (e.g., using lipids and other methods of transfection known in the art, see for example Beigelman et al, U.S. Pat. No. 6,395,713).

The term "short interfering nucleic acid," "short interfering RNA," "siRNA," "short interfering nucleic acid molecule," or "short interfering oligonucleotide molecule," or as used herein refers to any nucleic acid molecule capable of inhibiting or down regulating gene expression or viral replication, for example by mediating RNA interference "RNAi" or gene silencing in a sequence-specific manner. Non limiting examples of NA molecules of the invention are shown in FIG. 1. For example the NA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The NA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the NA is assembled from a single oligonucleotide, where the self-complementary sense and antisense regions of the NA are linked by means of a nucleic acid based or non-nucleic acid-based linker(s). The NA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

By "modulate" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

By "inhibit," "down-regulate," or "reduce," it is meant that the expression of the gene, or level of RNA molecules or equivalent RNA molecules encoding one or more proteins or protein subunits, or activity of one or more proteins or protein subunits, is reduced below that observed in the absence of the nucleic acid molecules of the invention. In one embodiment, inhibition, down-regulation or reduction with an NA molecule is below that level observed in the presence of an inactive or attenuated molecule. In another embodiment, inhibition, down-regulation, or reduction with NA molecules is below that level observed in the presence of, for example, an NA molecule with scrambled sequence or with mismatches. In another embodiment, inhibition, down-regulation, or reduction of gene expression with a nucleic acid molecule of the instant invention is greater in the presence of the nucleic acid molecule than in its absence.

By "gene" or "target gene" is meant a nucleic acid that encodes an RNA, for example, nucleic acid sequences including, but not limited to, structural genes encoding a polypeptide. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nuclear RNA (snRNA), ribosomal RNA (rRNA), transfer RNA (tRNA) and precursor RNAs thereof. Such non-coding RNAs can serve as target nucleic acid molecules for NA mediated RNA interference in modulating the activity of fRNA or ncRNA involved in functional or regulatory cellular processes. Aberrant fRNA or ncRNA activity leading to disease can therefore be modulated by NA molecules of the invention. NA molecules targeting fRNA and ncRNA can also be used to manipulate or alter the genotype or phenotype of an organism or cell, by intervening in cellular processes such as genetic imprinting, transcription, translation, or nucleic acid processing (e.g., transamination, methylation etc.).

By "homologous sequence" is meant, a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes, such as a cytokine and its corresponding receptors. A homologous sequence can be a nucleotide sequence that is shared by two or more non-coding polynucleotides, such as noncoding DNA or RNA, regulatory sequences, introns, and sites of transcriptional control or regulation. Homologous sequences can also include conserved sequence regions shared by more than one polynucleotide sequence. Homology does not need to be perfect homology (e.g., 100%), as partially homologous sequences are also contemplated by the instant invention (e.g., 99%, 98%, 97%, 96%, 95%, 94%, 93%, 92%, 91%, 90%, 89%, 88%, 87%, 86%, 85%, 84%, 83%, 82%, 81%, 80% etc.).

By "conserved sequence region" is meant, a nucleotide sequence of one or more regions in a polynucleotide does not vary significantly between generations or from one biological system or organism to another biological system or organism. The polynucleotide can include both coding and non-coding DNA and RNA.

By "sense region" is meant a nucleotide sequence of a NA molecule having complementarity to an antisense region of the NA molecule. In addition, the sense region of a NA molecule can comprise a nucleic acid sequence having homology with a target nucleic acid sequence.

By "antisense region" is meant a nucleotide sequence of a NA molecule having complementarity to a target nucleic acid sequence. In addition, the antisense region of a NA molecule can optionally comprise a nucleic acid sequence having complementarity to a sense region of the NA molecule.

By "target nucleic acid" is meant any nucleic acid sequence whose expression or activity is to be modulated. The target nucleic acid can be DNA or RNA.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence.

In one embodiment of the present invention, each sequence of a NA molecule of the invention is independently about 18 to about 24 nucleotides in length, in specific embodiments about 18, 19, 20, 21, 22, 23, or 24 nucleotides in length. In another embodiment, the NA duplexes of the invention independently comprise about 17 to about 23 base pairs (e.g., about 17, 18, 19, 20, 21, 22, or 23). In yet another embodiment, NA molecules of the invention comprising hairpin structures are about 35 to about 55 (e.g., about 35, 40, 45, 50 or 55) nucleotides in length, or about 38 to about 44 (e.g., about 38, 39, 40, 41, 42, 43, or 44) nucleotides in length and comprising about 16 to about 22 (e.g., about 16, 17, 18, 19, 20, 21 or 22) base pairs. Exemplary NA molecules of the invention are shown in FIG. 1 and Table 3.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats.

The NA molecules of the invention are added directly, or can be complexed with cationic lipids, packaged within liposomes, or otherwise delivered to target cells or tissues. The nucleic acid or nucleic acid complexes can be locally administered to relevant tissues ex vivo, or in vivo through direct application, or injection, with or without their incorporation in biopolymers. In particular embodiments, the nucleic acid molecules of the invention comprise sequences shown in FIG. 1 and Table 3. Examples of such nucleic acid molecules consist essentially of sequences defined in the figures and Tables.

By "subject" is meant an organism, which is a donor or recipient of explanted cells or the cells themselves. "Subject" also refers to an organism to which the nucleic acid molecules of the invention can be administered. A subject can be a mammal or mammalian cells, including human or human cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

```
human siRNA1 target (SEQ ID NO:1):
5'-AAC GTG TGC TAC GAT CAC TAC-3' mouse siRNA1 target (SEQ ID NO:2):
5'-AAT GTA TGC TAC GAC CAC CAC-3' human siRNA2 target (SEQ ID NO:3):
5'-AAG TTC ATC AAG GGG GAG ATA-3' mouse siRNA2 target (SEQ ID NO:4):
5'-AAG TTC ATG AAG GGA GAG ATA-3' human siRNA3 target (SEQ ID NO:5):
5'-AAG ACT GTC TTC ACA GTG TTC-3' mouse siRNA3 target (SEQ ID NO:87):
5'-AAG ACT GTC TTC ACC GTG TTT-3' human siRNA4 target (SEQ ID NO:6):
5'-AAGGAGGTGTGGGGAGATGAG-3'
```

Figure 2:
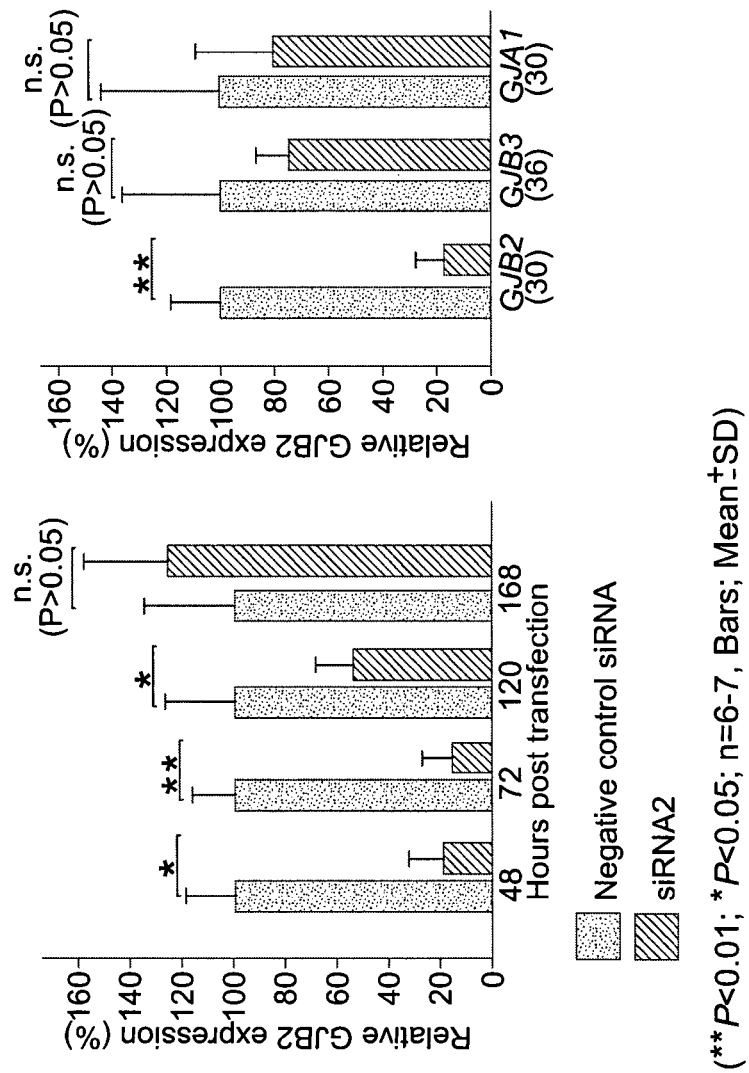

FIG. 2. GJB2 silencing in HEK293 cells. (A) Semiquantitative RT-PCR in HEK293 cells show suppression of GJB2 expression by more than 80% of control levels with siRNA2 and by approximately 50% of control levels with siRNA1 and siRNA3; siRNA4 was ineffective (72 h post transfection). PCR signals were quantified with 100 ng total RNA and thermocycles in exponential phase. GJB2 signals correlated with amount of total RNA added (range of RNA, 12.5-200 ng; r=0.808; p<0.001; n=36). (B) GJB2 silencing by siRNA2 was maximum at 72 h post transfection and returned to control level within 168 h. (C) siRNA2 did not affect expression levels of GJB3 and GJA1.

Figure 3:
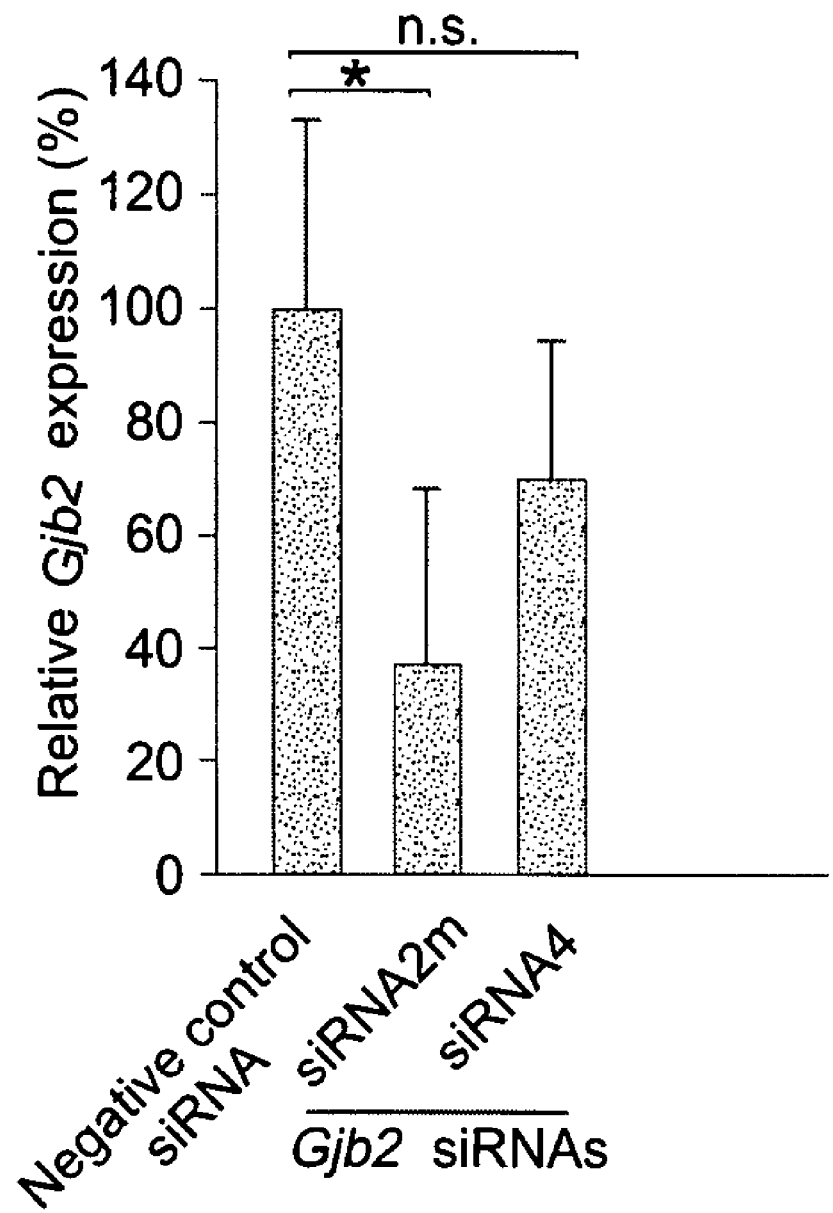

FIG. 3. Silencing of Gjb2 and GJB2$_{R75W}$-eGFP in P19 cells. siRNA2m suppressed endogenous Gjb2 mRNA (p<0.05; n=7) while siRNA4 exerted no effect (p=0.142; n=7).

Figure 4:
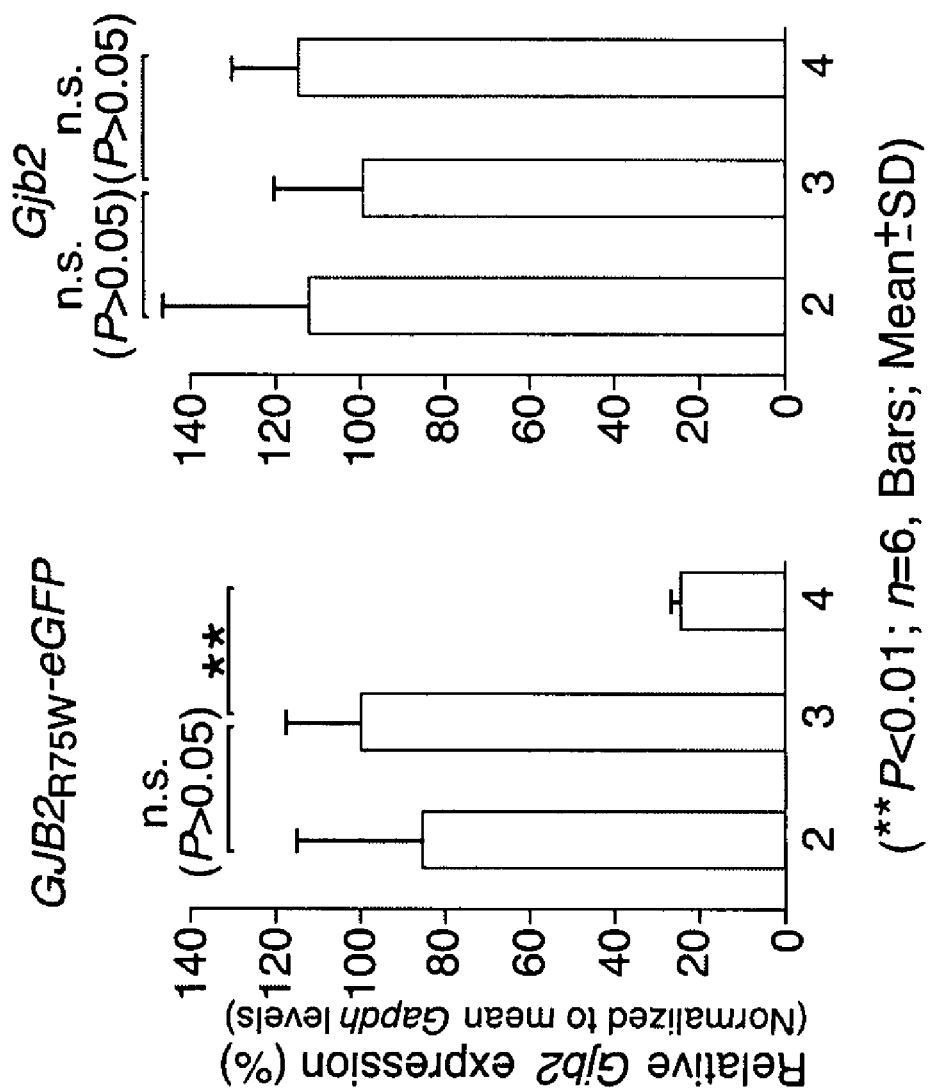

FIG. 4. siRNA2 prevented hearing loss associated with GJB2$_{R75W}$-eGFP expression in mice (n=8-10, for each group). The Sample groups are as follows in Table 1:

TABLE 1

| Sample group | Nucleic acids in liposome (1:1 DOTAP and cholesterol; 4 mM; 100 µl) |
|---|---|
| 1 | pGJB2$_{R75W}$-eGFP 25 µg |
| 2 | pGJB2$_{R75W}$-eGFP 25 µg + empty vector 25 µg |
| 3 | pGJB2$_{R75W}$-eGFP 25 µg + negative control siRNA 25 µg |
| 4 | pGJB2$_{R75W}$-eGFP 25 µg + siRNA 25 µg | pGJB2$_{R75W}$-eGFP (25 µg/100 µl lipocomplex) increased the intraaural difference in ABR thresholds as compared to empty vector controls (25 µg/100 µl) (p<0.05). There was no difference in thresholds in contralateral, untreated ears in each group (p=0.158, data not shown). Co-transfection of siRNA2 (25 µg/100 µl) with pGJB2$_{R75W}$-eGFP significantly reduced ABR threshold differences as compared to animals co-transfected with negative control siRNA (25 µg/100 µl) (p<0.05).

FIG. 5. Silencing of GJB2$_{R75W}$-eGFP transgene in mice. Expression of (a) GJB2$_{R75W}$-eGFP and (b) endogenous Gjb2 were quantified using 100 ng total RNA and thermocycles in exponential phase. Gapdh levels served as an internal standard. (c) siRNA2 reduced GJB2$_{R75W}$-eGFP mRNA to less than 30% of control levels without significant changes in endogenous Gjb2 expression.

Like reference symbols in the various drawings indicate like elements.

DETAILED DESCRIPTION

High suppression potency and sequence specificity of even single nucleotide resolution has encouraged the development of RNAi-based therapeutic models for possible use in viral infections and cancer. This approach is also particularly attractive for dominant genetic diseases in which mutant proteins cause an inhibitory or toxic effect, as in spinocerebellar ataxia types 1 and 3, spinobulbar muscular atrophy, and slow channel congenital myasthenic syndrome.

Several genes are known to be involved in causing deafness as a result of a dominant negative mechanism of action, and are shown in Table 2 below.

TABLE 2

| Deafness Locus | Gene | Description of Gene |
|---|---|---|
| DFNA2 | KCNQ4 | Official Symbol: KCNQ4 and Name: potassium voltage-gated channel, KQT-like subfamily, member 4 [Homo sapiens]<br>Other Aliases: HGNC: 6298, DFNA2, KV7.4<br>Other Designations: potassium channel KQT-like 4; potassium voltage-gated channel KQT-like protein 4<br>Chromosome: 1; Location: 1p34<br>GeneID: 9132 |
| DFNA3 | GJB2 | Official Symbol: GJB2 and Name: gap junction protein, beta 2, 26 kDa (connexin 26) [Homo sapiens]<br>Other Aliases: HGNC: 4284, CX26, DFNA3, DFNB1, HID, KID, NSRD1, PPK<br>Other Designations: gap junction protein beta 2; gap junction protein, beta 2, 26 kD (connexin 26)<br>Chromosome: 13; Location: 13q11-q12<br>GeneID: 2706 |
| DFNA3 | GJB6 | Official Symbol: GJB6 and Name: gap junction protein, beta 6 (connexin 30) [Homo sapiens]<br>Other Aliases: HGNC: 4288, CX30, DFNA3, ED2, EDH, HED<br>Other Designations: connexin 30; ectodermal dysplasia 2, hidrotic (Clouston syndrome)<br>Chromosome: 13; Location: 13q12<br>GeneID: 10804 |
| DFNA5 | DFNA5 | Official Symbol: DFNA5 and Name: deafness, autosomal dominant 5 [Homo sapiens]<br>Other Aliases: HGNC: 2810, ICERE-1<br>Other Designations: deafness, autosomal dominant 5 protein; nonsyndromic hearing impairment protein<br>Chromosome: 7; Location: 7p15<br>GeneID: 1687 |

A. Generating siRNA

A "small interfering RNA" or "short interfering RNA" or "siRNA" or "short hairpin RNA" or "shRNA" is a double-stranded RNA molecule that is complementary to a target nucleic acid sequence, for example, GJB2. A double-stranded RNA molecule is formed by the complementary pairing between a first RNA portion and a second RNA portion. The length of each portion generally is less than 30 nucleotides in length (e.g., 29, 28, 27, 26, 25, 24, 23, 22, 21, 20, 19, 18, 17, 16, 15, 14, 13, 12, 11, or 10 nucleotides). In some embodiments, the length of each portion is 19 to 25 nucleotides in length. In some siRNA molecules, the complementary first and second portions of the RNA molecule are the "stem" of a hairpin structure. The two portions can be joined by a linking sequence, which can form the "loop" in the hairpin structure. The linking sequence can vary in length. In some embodiments, the linking sequence can be 5, 6, 7, 8, 9, 10, 11, 12 or 13 nucleotides in length. A representative linking sequence is 5'-TTC AGA AGG-3' (SEQ ID NO:86), but any of a number of sequences can be used to join the first and second portions. The first and second portions are complementary but may not be completely symmetrical, as the hairpin structure may contain 3' or 5' overhang nucleotides (e.g., a 1, 2, 3, 4, or 5 nucleotide overhang).

RNA molecules have been shown by many researchers to be effective in suppressing mRNA accumulation. siRNA-mediated suppression of nucleic acid expression is specific as even a single base pair mismatch between siRNA and the targeted nucleic acid can abolish the action of RNA interference. siRNAs generally do not elicit anti-viral responses.

There are many programs to generate siRNAs that are predicted to be effective in down-regulating target genes. Several rules are applied. To target the mRNA of interest (i.e., the transcribed gene of interest), the antisense strand of the siRNA must preferentially bind with the mRNA of interest. On that basis, low stability at the 5' end of the antisense strand and high stability at the 5' end of the sense strand is desired. Low stability at the 5' of the antisense strand will allow it to incorporate into RISC and minimize the incorporation of the sense strand into RISC. In addition, an area of low stability in the mid region of the construct should be included to promote cleavage of mRNA. Each of the small interfering RNAs should have a GC content of about 45-55%, include 19-20 nucleotides in the duplex, and have a two nucleotide overhang at the 3' ends. BLAST analysis should reveal no cognate matches to nonspecific mRNAs.

Once designed, the siRNAs of the present invention can be generated by any method known in the art, for example, by in vitro transcription, recombinantly, or by synthetic means (e.g., having either a TT or a UU overhang at the 3' end). siRNAs can be generated in vitro by using a recombinant enzyme, such as T7 RNA polymerase, and DNA oligonucleotide templates, or can be prepared in vivo, for example, in cultured cells (see, for example, Lee et al., 2002, *Nat. Biotech.*, 20:500-5).

In addition, strategies have been described for producing a hairpin siRNA from vectors containing a RNA polymerase III promoter. Various vectors have been constructed for generating hairpin siRNAs in host cells using either an H1-RNA or an snU6 RNA promoter. A RNA molecule as described above (e.g., a first portion, a linking sequence, and a second portion) can be operably linked to such a promoter. When transcribed by RNA polymerase III, the first and second portions form a duplexed stem of a hairpin and the linking sequence forms a loop. The pSuper vector (OligoEngines Ltd., Seattle, Wash.) also can be used to generate siRNA.

A TTTTT penta-nucleotide usually is attached to the end of the second portion (i.e., the antisense strand) in a vector to serve as a terminator for RNA polymerase III transcription. For that reason, siRNA candidates that contain more than three consecutive Ts should be avoided since four or more consecutive Ts in the template nucleic acid triggers termination of RNA polymerase III transcription.

Several techniques can be used to test the effect of different siRNA constructs on cellular mRNA and/or protein levels. For example, dual-GFP transfection, CHO-cell double transfection based on an antibody/epitope specificity, quantitative RT-PCR, Northern blots, Western blots, immunofluorescence, and Hygro/Neo selection. These methods are well known in the art.

B. Nucleic Acids

As used herein, the term "nucleic acid molecule" can include DNA molecules and RNA molecules and analogs of a DNA or RNA molecule generated using nucleotide analogs. A nucleic acid molecule of the invention can be single-stranded or double-stranded, and the strandedness will depend upon its intended use. Fragments or portions of the disclosed nucleotide sequences are also encompassed by the present invention. By "fragment" or "portion" is meant less than full length of the nucleotide sequence.

The invention further encompasses nucleic acid molecules that differ in nucleotide sequence. Nucleic acid molecules that differ in sequence from the original nucleic acid sequence can be generated by standard techniques, such as site-directed mutagenesis, PCR-mediated mutagenesis, or oligonucleotide-mediated mutagenesis. In addition, nucleotide changes can be introduced randomly along all or part of a nucleic acid molecule such as by saturation mutagenesis. Alternatively, nucleotide changes can be introduced into a sequence by chemically synthesizing a nucleic acid molecule having such changes.

To calculate percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

The alignment of two or more sequences to determine percent sequence identity may be performed using the algorithm described by Altschul et al. (1997, *Nucleic Acids Res.*, 25:3389-402) as incorporated into BLAST (basic local alignment search tool) programs, available at ncbi.nlm.nih.gov on the World Wide Web. BLAST searches can be performed to determine percent sequence identity between a nucleic acid molecule of the invention and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence of the invention and another sequence, the default parameters of the respective programs are used. Sequence analysis of nucleic acid sequences can be performed used BLAST version 2.2.9 (updated on May 12, 2004).

As used herein, an "isolated" nucleic acid molecule is a nucleic acid molecule that is separated from other nucleic acid molecules that are usually associated with the isolated nucleic acid molecule. Thus, an "isolated" nucleic acid molecule includes, without limitation, a nucleic acid molecule that is free of sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA, or genomic library) or a portion of a gel (e.g., agarose, or polyacrylamine) containing restriction-digested genomic DNA is not to be considered an isolated nucleic acid.

Isolated nucleic acid molecules of the invention can be obtained using techniques routine in the art. For example, isolated nucleic acids within the scope of the invention can be obtained using any method including, without limitation, recombinant nucleic acid technology, and/or the polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid molecule of the invention. Isolated nucleic acids of the invention also can be chemically synthesized, either as a single nucleic acid molecule or as a series of oligonucleotides. In addition, isolated nucleic acid molecules of the invention also can be obtained by mutagenesis using common molecular cloning techniques (e.g., site-directed mutagenesis). Possible mutations include, without limitation, deletions, insertions, substitutions, and combinations thereof.

Vectors containing nucleic acid molecules also are provided by the invention. Vectors, including expression vectors, suitable for use in the present invention are commercially available and/or produced by recombinant DNA technology methods routine in the art. A vector containing a nucleic acid molecule can have elements necessary for expression operably linked to such a nucleic acid, and further can include sequences such as those encoding a selectable marker (e.g., a sequence encoding antibiotic resistance), and/or those that can be used in purification of a polypeptide (e.g., a His tag). A "vector" is defined to include any viral vector, as well as any plasmid, cosmid, phage, or binary vector. Vectors can integrate into the cellular genome or exist extrachromosomally (e.g., an autonomous replicating plasmid with an origin of replication).

Elements necessary for expression include nucleic acid sequences that direct and regulate expression of nucleic acid coding sequences. One example of an element necessary for expression is a promoter sequence. Examples of promoters that may be used in the present invention include the mouse U6 RNA promoters, synthetic human H1RNA promoters, SV40, CMV, RSV, RNA polymerase II, and RNA polymerase III promoters. Elements necessary for expression also can include ribosome-binding sites, introns, enhancer sequences, response elements, or inducible elements that modulate expression of a nucleic acid. Elements necessary for expression can be of bacterial, yeast, insect, mammalian, or viral origin and vectors can contain a combination of elements from different origins. Elements necessary for expression are described, for example, in Goeddel, 1990, *Gene Expression Technology: Methods in Enzymology*, 185, Academic Press, San Diego, Calif. As used herein, operably linked means that a promoter and/or other regulatory element(s) are positioned in a vector relative to a nucleic acid in such a way as to direct or regulate expression of the nucleic acid. A nucleic acid can be operably-linked to regulatory sequences in sense or anti-sense orientation. For example, in the case of siRNA constructs, expression may refer to the transcription of the siRNA only. In addition, expression can refer to the transcription of sense mRNA and may also refer to the production of protein.

In one embodiment of the present invention, a vector contains an H1-RNA promoter that is operably linked to a nucleic acid sequence encoding a siRNA. Thus, the H1-RNA promoter initiates the transcription of the siRNA. In another embodiment, the promoter is regulatable, providing inducible expression of the siRNA.

Another aspect of the invention pertains to host cells into which a vector of the invention, e.g., an expression vector, or an isolated nucleic acid molecule of the invention has been introduced. The term "host cell" refers not only to the particular cell but also to the progeny or potential progeny of such a cell. A host cell can be any prokaryotic or eukaryotic cell. For example, host cells can include bacterial cells such as *E. coli*, insect cells, yeast cells, or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, calcium phosphate precipitation, electroporation, heat shock, lipofection, microinjection, and viral-mediated nucleic acid transfer.

C. Expression of Nucleic Acid Molecules of the Invention

Certain NA molecules of the instant invention can be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; Dropulic et al., 1992, J. Virol., 66, 1432-41; Weerasinghe et al., 1991, J. Virol., 65, 55314; Ojwang et al., 1992, Proc. Natl. Acad. Sci. USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45). Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J. Biol. Chem., 269, 25856).

RNA molecules of the present invention can be expressed from transcription units (see for example Couture et al., 1996, TIG., 12, 510) inserted into DNA or RNA vectors. The recombinant vectors can be DNA plasmids or viral vectors. NA expressing viral vectors can be constructed based on, but not limited to, adeno-associated virus, retrovirus, adenovirus, or alphavirus. In another embodiment, pol III based constructs are used to express nucleic acid molecules of the invention (see for example Thompson, U.S. Pats. Nos. 5,902,880 and 6,146,886). The recombinant vectors capable of expressing the NA molecules can be delivered as described above, and persist in target cells. Alternatively, viral vectors can be used that provide for transient expression of nucleic acid molecules. Such vectors can be repeatedly administered as necessary. Once expressed, the NA molecule interacts with the target mRNA and generates an RNAi response. Delivery of NA molecule expressing vectors can be systemic, such as by intravenous or intramuscular administration, by administration to target cells ex-planted from a subject followed by reintroduction into the subject, or by any other means that would allow for introduction into the desired target cell (for a review see Couture et al., 1996, TIG., 12, 510).

In one aspect the invention features an expression vector comprising a nucleic acid sequence encoding at least one NA molecule of the instant invention. The expression vector can encode one or both strands of a NA duplex, or a single self-complementary strand that self hybridizes into a NA duplex. The nucleic acid sequences encoding the NA molecules of the instant invention can be operably linked in a manner that allows expression of the NA molecule (see for example Paul et al., 2002, Nature Biotechnology, 19, 505; Miyagishi and Taira, 2002, Nature Biotechnology, 19, 497; Lee et al., 2002, Nature Biotechnology, 19, 500).

Transcription of the NA molecule sequences can be driven from a promoter for eukaryotic RNA polymerase I (pol I), RNA polymerase II (pol II), or RNA polymerase III (pol III). Transcripts from pol II or pol III promoters are expressed at high levels in all cells. The levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA, 87, 6743-7; Gao and Huang 1993, Nucleic Acids Res., 21, 2867-72; Lieber et al., 1993, Methods Enzymol., 217, 47-66; Zhou et al., 1990, Mol. Cell. Biol., 10, 4529-37). Several investigators have demonstrated that nucleic acid molecules expressed from such promoters can function in mammalian cells (e.g. Kashani-Sabet et al., 1992, Antisense Res. Dev., 2, 3-15; Ojwang et al., 1992, Proc. Natl. Acad. Sci. USA, 89, 10802-6; Chen et al., 1992, Nucleic Acids Res., 20, 4581-9; Yu et al., 1993, Proc. Natl. Acad. Sci. USA, 90, 6340-4; L'Huillier et al., 1992, EMBO J, 11, 4411-8; Lisziewicz et al., 1993, Proc. Natl. Acad. Sci. U S. A, 90, 80004; Thompson et al., 1995, Nucleic Acids Res., 23, 2259; Sullenger & Cech, 1993, Science, 262, 1566). More specifically, transcription units such as the ones derived from genes encoding U6 small nuclear (snRNA), transfer RNA (tRNA) and adenovirus VA RNA are useful in generating high concentrations of desired RNA molecules such as NA in cells (Thompson et al., supra; Couture and Stinchcomb, 1996, supra; Noonberg et al., 1994, Nucleic Acid Res., 22, 2830; Noonberg et al., U.S. Pat. No. 5,624,803; Good et al., 1997, Gene Ther., 4, 45; Beigelman et al., International PCT Publication No. WO 96/18736. The above NA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

D. Detection of Nucleic Acids and Polypeptides

Nucleic acid molecules and polypeptides can be detected using a number of different methods. Methods for detecting nucleic acids include, for example, PCR and nucleic acid hybridizations (e.g., Southern blot, Northern blot, or in situ hybridizations). Specifically, oligonucleotides (e.g., oligonucleotide primers) capable of amplifying a target nucleic acid can be used in a PCR reaction. PCR methods generally include the steps of obtaining a sample, isolating nucleic acid (e.g., DNA, RNA, or both) from the sample, and contacting the nucleic acid with one or more oligonucleotide primers that hybridize(s) with specificity to the template nucleic acid under conditions such that amplification of the template nucleic acid occurs. In the presence of a template nucleic acid, an amplification product is produced. Conditions for amplification of a nucleic acid and detection of an amplification product are known to those of skill in the art (see, e.g., PCR Primer: A Laboratory Manual, 1995, Dieffenbach & Dveksler, Eds., Cold Spring Harbor Laboratory Press, Cold Spring Harbor, N.Y.; and U.S. Pat. Nos. 4,683,195; 4,683,202; 4,800, 159; and 4,965,188). Modifications to the original PCR also have been developed. For example, anchor PCR, RACE PCR, RT-PCR, or ligation chain reaction (LCR) are additional PCR methods known in the art (see, e.g., Landegran et al., 1988, Science, 241:1077-1080; and Nakazawa et al., 1994, Proc. Natl. Acad. Sci. USA, 91:360-364).

As used herein, "standard amplification conditions" refer to the basic components of an amplification reaction mix, and cycling conditions that include multiple cycles of denaturing the template nucleic acid, annealing the oligonucleotide primers to the template nucleic acid, and extension of the primers by the polymerase to produce an amplification product (see, for example, U.S. Pat. Nos. 4,683,195; 4,683,202; 4,800,159; and 4,965,188). The basic components of an amplification reaction mix generally include, for example, about 10-25 nmole of each of the four deoxynucleoside triphosphates, (e.g., dATP, dCTP, dTTP, and dGTP, or analogs thereof), 10-100 pmol of each primer, template nucleic acid, and a polymerase enzyme. The reaction components are generally suspended in a buffered aqueous solution having a pH of between about 7 and about 9. The aqueous buffer can further include one or more co-factors (e.g., $Mg^{2+}$, $K^+$) required by the polymerase. Additional components such as DMSO are optional. Template nucleic acid is typically denatured at a temperature of at least about 90° C., and extension from primers is typically performed at a temperature of at least about 72° C.

The annealing temperature can be used to control the specificity of amplification. The temperature at which primers anneal to template nucleic acid must be below the $T_m$ of each of the primers, but high enough to avoid non-specific annealing of primers to the template nucleic acid. The $T_m$ is the temperature at which half of the DNA duplexes have separated into single strands, and can be predicted for an oligonucleotide primer using the formula provided in section 11.46 of Sambrook et al. (1989, Molecular Cloning: A Laboratory Manual, 2nd Ed., Cold Spring Harbor Laboratory Press, Cold Spring Harbor, N.Y.). Non-specific amplification products are detected as bands on a gel that are not the size expected for the correct amplification product. It can be appreciated by those of skill in the art that appropriate positive and negative controls should be performed with every set of amplification reactions to avoid uncertainties related to contamination and/ or non-specific annealing of oligonucleotide primers and extension therefrom.

A pair of primers in an amplification reaction must anneal to opposite strands of the template nucleic acid, and should be an appropriate distance from one another such that the polymerase can effectively polymerize across the region and such that the amplification product can be readily detected using, for example, electrophoresis. Oligonucleotide primers can be designed using, for example, a computer program such as OLIGO (Molecular Biology Insights Inc., Cascade, Colo.) to assist in designing primers that have similar melting temperatures. Typically, oligonucleotide primers are 10 to 30 or 40 or 50 nucleotides in length (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length), but can be longer or shorter if appropriate amplification conditions are used. Oligonucleotides of the invention can be obtained by restriction enzyme digestion of a nucleic acid molecule or can be prepared by standard chemical synthesis and other known techniques.

Alternatively, a nucleic acid can be detected using a labeled oligonucleotide probe capable of hybridizing to nucleic acids on a Southern blot. In the presence of homologous nucleic acid, a hybridization complex is produced between the nucleic acid and the oligonucleotide probe. Hybridization between nucleic acid molecules is discussed in detail in Sambrook et al. (1989, *Molecular Cloning: A Laboratory Manual*, 2$^{nd}$ Ed., Cold Spring Harbor Laboratory Press, Cold Spring Harbor, N.Y.; Sections 7.37-7.57, 9.47-9.57, 11.7-11.8, and 11.45-11.57).

For oligonucleotide probes less than about 100 nucleotides, Sambrook et al. discloses suitable Southern blot conditions in Sections 11.45-11.46. The $T_m$ between a sequence that is less than 100 nucleotides in length and a second sequence can be calculated using the formula provided in Section 11.46. Sambrook et al. additionally discloses prehybridization and hybridization conditions for a Southern blot that uses oligonucleotide probes greater than about 100 nucleotides (see Sections 9.47-9.52). Hybridizations with an oligonucleotide greater than 100 nucleotides generally are performed 15-25° C. below the $T_m$. The $T_m$ between a sequence greater than 100 nucleotides in length and a second sequence can be calculated using the formula provided in Sections 9.50-9.51 of Sambrook et al. Additionally, Sambrook et al. recommends the conditions indicated in Section 9.54 for washing a Southern blot that has been probed with an oligonucleotide greater than about 100 nucleotides.

The conditions under which membranes containing nucleic acids are prehybridized and hybridized, as well as the conditions under which membranes containing nucleic acids are washed to remove excess and non-specifically bound probe can play a significant role in the stringency of the hybridization. Such hybridizations can be performed, where appropriate, under moderate or high stringency conditions. Such conditions are described, for example, in Sambrook et al. section 11.45-11.46. For example, washing conditions can be made more stringent by decreasing the salt concentration in the wash solutions and/or by increasing the temperature at which the washes are performed. In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium.

It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a target nucleic acid but not to a non-homologous nucleic acid if hybridization to the homologous target nucleic acid is at least 5-fold (e.g., at least 6-fold, 7-fold, 8-fold, 9-fold, 10-fold, 20-fold, 50-fold, or 100-fold) greater than hybridization to the non-homologous nucleic acid. The amount of hybridization can be quantitated directly on a membrane or from an autoradiograph using, for example, a PhosphorImager or a Densitometer (Molecular Dynamics, Sunnyvale, Calif.).

Detection of an amplification product or a hybridization complex is usually accomplished using detectable labels. The term "label" with regard to a nucleic acid is intended to encompass direct labeling of a nucleic acid by coupling (i.e., physically linking) a detectable substance to the nucleic acid, as well as indirect labeling of the nucleic acid by reactivity with another reagent that is directly labeled with a detectable substance. Detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H. An example of indirect labeling includes end-labeling a nucleic acid with biotin such that it can be detected with fluorescently labeled streptavidin.

E. Examples of Mutations

KCNQ4

1. DEAFNESS, AUTOSOMAL DOMINANT NONSYNDROMIC SENSORINEURAL 2 [KCNQ4, GLY285SER] In a family with DFNA2, a gly285-to-ser (GGC-to-AGC) mutation has been identified in KCNQ4 in heterozygous state. This mutation segregated with all affected members in the pedigree and was not found on 150 control Caucasian chromosomes.

2. DEAFNESS, AUTOSOMAL DOMINANT NONSYNDROMIC SENSORINEURAL 2 [KCNQ4, TRP276SER] In Dutch and Japanese families with DFNA2, an 827G-C transversion in exon 5 of the KCNQ4 gene has been identified that results in a trp276-to-ser (W276S) mutation in the pore region of the protein.

3. DEAFNESS, AUTOSOMAL DOMINANT NONSYNDROMIC SENSORINEURAL 2 [KCNQ4, GLY321SER] In a family with DFNA2, a 961G-A transition in exon 7 of the KCNQ4 gene has been identified, which produces a gly321-to-ser change in the S6 transmembrane domain of the protein.

4. DEAFNESS, AUTOSOMAL DOMINANT NONSYNDROMIC SENSORINEURAL 2 [KCNQ4, GLY285CYS] In American and French families with DFNA2, an 853G-T transversion in exon 6 of the KCNQ4 gene has been identified that results in a gly285-to-cys substitution.

5. DEAFNESS, AUTOSOMAL DOMINANT NONSYNDROMIC SENSORINEURAL 2 [KCNQ4, 13-BP DEL, NT211] In a Belgian family with DFNA2, a 13 bp deletion between nucleotide positions 211 and 224 of the KCNQ4 cDNA sequence has been identified. This deletion results in a frameshift after gly70, followed by 63 novel amino acids and a premature stop codon at amino acid position 134. The mutation yields a KCNQ4 protein that is truncated before the first transmembrane region.

6. DEAFNESS, AUTOSOMAL DOMINANT NONSYNDROMIC SENSORINEURAL 2 [KCNQ4, LEU281SER] In an American family, a leu281-to-ser missense mutation resulting from a T-to-C transition at position 842 of the KCNQ4 gene has been identified.

7. DEAFNESS, AUTOSOMAL DOMINANT NONSYNDROMIC SENSORINEURAL 2 [KCNQ4, LEU274HIS] In a Dutch family, a leu274-to-his (L274H) mutation in the KCNQ4 gene has been identified.

GJB2

1. DEAFNESS, AUTOSOMAL DOMINANT NONSYNDROMIC SENSORINEURAL 3 [GJB2, MET34THR] The M34T allele of GJB2 may be associated with autosomal dominant hearing.

2. DEAFNESS, AUTOSOMAL DOMINANT NONSYNDROMIC SENSORINEURAL 3 [GJB2, ARG75TRP] The Arg75Trp allele of GJB2 is associated with autosomal dominant hearing.

3. VOHWINKEL SYNDROME [GJB2, ASP66HIS] Vohwinkle syndrome is the characterized by mutilating palmoplantar keratoderma (PPK) associated with honeycomb-like keratoderma and starfish-like keratoses on the knuckles. There is also hearing loss.

4. KERATODERMA, PALMOPLANTAR, WITH DEAFNESS [GJB2, GLY59ALA] Autosomal dominant deafness and palmoplantar keratoderma can be caused by a G-to-C transversion at nucleotide 175 of the GJB2 gene resulting in the substitution of an alanine residue for a glycine residue at codon 59.

5. DEAFNESS, AUTOSOMAL DOMINANT NONSYNDROMIC SENSORINEURAL 3 [GJB2, ARG143GLN] A G-to-A transition that results in an arg143-to-gln (R143Q) substitution in the GJB2 gene can cause autosomal dominant nonsyndromic deafness.

6. DEAFNESS, AUTOSOMAL DOMINANT NONSYNDROMIC SENSORINEURAL 3 [GJB2, CYS202PHE] Late childhood onset of autosomal dominant isolated hearing loss can be caused by a heterozygous G-to-T transversion at nucleotide 605 of the GJB2 gene, resulting in the substitution of a cysteine residue by a phenylalanine residue at codon 202 in the fourth transmembrane domain of the CX26 protein. Hearing loss is detected between 10 and 20 years of age. There is significant variability for the severity of the hearing loss.

7. DEAFNESS, AUTOSOMAL DOMINANT NONSYNDROMIC SENSORINEURAL 3 [GJB2, TRP44CYS] Early-onset severe to profound nonsyndromic hearing loss can segregate with a trp44-to-cys (W44C) mutation in the GJB2 gene.

8. KERATITIS-ICHTHYOSIS-DEAFNESS SYNDROME, AUTOSOMAL DOMINANT [GJB2, ASP50ASN] Keratitis-ichthyosis-deafness syndrome can be caused by a 148G-A transition in the GJB2 gene, resulting in an asp50-to-asn (D50N) substitution. This mutation occurs in the highly conserved first extracellular loop of CX26, which is crucial for voltage gating and connexon-connexon interactions.

9. KERATITIS-ICHTHYOSIS-DEAFNESS SYNDROME [GJB2, GLY12ARG] Keratitis-ichthyosis-deafness syndrome can be caused by a heterozygous G-to-C transversion in codon 12 of the GJB2 gene, replacing glycine with arginine (gly12 to arg; G12R) in CX26.

10. KERATITIS-ICHTHYOSIS-DEAFNESS SYNDROME [GJB2, SER17PHE] Keratitis-ichthyosis-deafness syndrome can be caused by a 50C-T transition in the GJB2 gene, leading to substitution of serine-17 with phenylalanine (ser17 to phe; S17F).

11. KERATODERMA, PALMOPLANTAR, WITH DEAFNESS [GJB2, ARG75GLN] Profound hearing loss and palmoplantar keratoderma can be caused by a 224G-A transition in the GJB2 gene resulting in an arg75-to-gln (R75Q) mutation. The age of onset and progression of hearing loss are variable among affected persons.

12. KERATITIS-ICHTHYOSIS-DEAFNESS SYNDROME [GJB2, ASP50TYR] Keratitis-ichthyosis-deafness syndrome can be caused by a transversion mutation, 148G-T, in GJB2 exon 2, resulting in a putative amino acid change from aspartic acid to tyrosine at codon 50 (D50Y).

13. DEAFNESS, AUTOSOMAL DOMINANT NONSYNDROMIC SENSORINEURAL 3 [GJB2, ASP179ASN] Autosomal dominant nonsyndromic postlingual hearing loss can be caused by a heterozygous 535G-A transition in the GJB2 gene, resulting in an asp179-to-asn (D179N) substitution that occurs in the second extracellular domain.

14. DEAFNESS, AUTOSOMAL DOMINANT NONSYNDROMIC SENSORINEURAL 3 [GJB2, TRP44SER] Autosomal dominant nonsyndromic postlingual hearing loss can be caused by a trp44-to-ser (W44S) mutation in the GJB2 gene.

GJB6

1. DEAFNESS, AUTOSOMAL DOMINANT NONSYNDROMIC SENSORINEURAL 3 [GJB6, THR5MET] An Italian family with autosomal dominant, bilateral, middle to high frequency hearing loss has been described in which affected members have a thr5-to-met substitution.

DFNA5

1. DEAFNESS, AUTOSOMAL DOMINANT NONSYNDROMIC SENSORINEURAL 5 [DFNA5, INV/DEL, EX8DEL] The absence of exon 8 results in a frameshift starting at amino acid 330, which introduces an aberrant stretch of 41 amino acids followed by a stop codon that prematurely truncates the protein.

2. DEAFNESS, AUTOSOMAL DOMINANT NONSYNDROMIC SENSORINEURAL 5 [DFNA5, 3-BP DEL, 372CTT] The CTT deletion in the polypyrimidine tract of intron 7 leads to skipping of exon 8 of DFNA5.

3. DEAFNESS, AUTOSOMAL DOMINANT NONSYNDROMIC SENSORINEURAL 5 [DFNA5, IVS7, C-G, –6] A 1200C-G transversion at position –6 of the splice acceptor site of intron 7 of the DFNA5 gene results in skipping of exon 8, which leads to 41 aberrant codons followed by a premature stop codon.

Appropriate siRNAs to target autosomal dominant nonsyndromic deafness caused by a dominant-negative mechanism of action are found in Table 3 below.

TABLE 3

| Gene | Targeted Mutation | siRNA Target Sequences (sense stand) |
| --- | --- | --- |
| KCNQ4 | Gly28Ser | a. CAACCATCAGCTATGGTGACA (SEQ ID NO:9)<br>b. ACAACCATCAGCTATGGTGAC (SEQ ID NO:10)<br>c. GACAACCATCAGCTATGGTGA (SEQ ID NO:11) |
|  | Trp276Ser | a. GCTCTGGTCGGGGACGATTAC (SEQ ID NO:12)<br>b. CGCTCTGGTCGGGGACGATTA (SEQ ID NO:13)<br>c. ACGCTCTGGTCGGGGACGATT (SEQ ID NO:14) |
|  | Gly321Ser | a. TAGGCTCCAGCTTTGCCCTGA (SEQ ID NO:15)<br>b. CTAGGCTCCAGCTTTGCCCTG (SEQ ID NO:16)<br>c. CCTAGGCTCCAGCTTTGCCCT (SEQ ID NO:17) |
|  | Gly285Cys | a. CAACCATCTGCTATGGTGACA (SEQ ID NO:18)<br>b. ACAACCATCTGCTATGGTGAC (SEQ ID NO:19)<br>c. GACAACCATCTGCTATGGTGA (SEQ ID NO:20) |

TABLE 3-continued

| Gene | Targeted Mutation | siRNA Target Sequences (sense stand) |
|---|---|---|
| | 13bp-del, NT211 | a. GCCTGCGGCCCGCGCACAAGC (SEQ ID NO:21)<br>b. CGCCTGCGGCCCGCGCACAAG (SEQ ID NO:22)<br>c. CCGCCTGCGGCCCGCGCACAA (SEQ ID NO:23) |
| | Leu281Ser | a. GATTACATCGACAACCATCGG (SEQ ID NO:24)<br>b. CGATTACATCGACAACCATCG (SEQ ID NO:25)<br>c. ACGATTACATCGACAACCATC (SEQ ID NO:26) |
| | Leu274His | a. CGACTCGCACTGGTGGGGAC (SEQ ID NO:27)<br>b. CCGACTCGCACTGGTGGGGA (SEQ ID NO:28)<br>c. GCCGACTCGCACTGGTGGGG (SEQ ID NO:29) |
| GJB2 | Met34Thr | a. TCGCATTACGATCCTCGTTGT (SEQ ID NO:30)<br>b. TTCGCATTACGATCCTCGTTG (SEQ ID NO:31)<br>c. TTTCGCATTACGATCCTCGTT (SEQ ID NO:32) |
| | Arg75Trp | a. CCCACATCTGGCTATGGGCCC (SEQ ID NO:33)<br>b. TCCCACATCTGGCTATGGGCC (SEQ ID NO:34)<br>c. CTCCCACATCTGGCTATGGGC (SEQ ID NO:35) |
| | Asp66His | a. TGTGCTACCATCACTACTTCC (SEQ ID NO:36)<br>b. GTGTGCTACCATCACTACTTC (SEQ ID NO:37)<br>c. CGTGTGCTACCATCACTACTT (SEQ ID NO:38) |
| | Gly59Ala | a. GCAGCCAGCCTGCAAGAACGT (SEQ ID NO:39)<br>b. TGCAGCCAGCCTGCAAGAACG (SEQ ID NO:40)<br>c. CTGCAGCCAGCCTGCAAGAAC (SEQ ID NO:41) |
| | Arg143Gln | a. CTTCTTCCAGGTCATCTTCGA (SEQ ID NO:42)<br>b. TCTTCTTCCAGGTCATCTTCG (SEQ ID NO:43)<br>c. ATCTTCTTCCAGGTCATCTTC (SEQ ID NO:44) |
| | Cys202Phe | a. TGGAATTTTCATCCTGCTGAA (SEQ ID NO:45)<br>b. CTGGAATTTTCATCCTGCTGA (SEQ ID NO:46)<br>c. TCTGGAATTTTCATCCTGCTG (SEQ ID NO:47) |
| | Trp44Cys | a. GAGGTGTGCGGAGATGAGCAG (SEQ ID NO:48)<br>b. GGAGGTGTGCGGAGATGAGCA (SEQ ID NO:49)<br>c. AGGAGGTGTGCGGAGATGAGC (SEQ ID NO:50) |
| | Asp50Asn | a. AGCAGGCCAACTTTGTCTGCA (SEQ ID NO:51)<br>b. GAGCAGGCCAACTTTGTCTGC (SEQ ID NO:52)<br>c. TGAGCAGGCCAACTTTGTCTG (SEQ ID NO:53) |
| | Gly12Arg | a. TCCTGGGGCGTGTGAACAAAC (SEQ ID NO:54)<br>b. ATCCTGGGGCGTGTGAACAAA (SEQ ID NO:55)<br>c. GATCCTGGGGCGTGTGAACAA (SEQ ID NO:56) |
| | Ser17Phe | a. CAAACACTTCACCAGCATTGG (SEQ ID NO:57)<br>b. CAAACACTTCACCAGCATTG (SEQ ID NO:58)<br>c. CAAACACTTCACCAGCATT (SEQ ID NO:59) |
| | Arg75Gln | a. CCACATCCAGCTATGGGCCCT (SEQ ID NO:60)<br>b. CCCACATCCAGCTATGGGCCC (SEQ ID NO:61)<br>c. TCCCACATCCAGCTATGGGCC (SEQ ID NO:62) |
| | Asp50Tyr | a. AGCAGGCCTACTTTGTCTGCA (SEQ ID NO:63)<br>b. GAGCAGGCCTACTTTGTCTGC (SEQ ID NO:64)<br>c. TGAGCAGGCCTACTTTGTCTG (SEQ ID NO:65) |
| | Asp179Asn | a. ACACTGTGAACTGCTTTGTGT (SEQ ID NO:66)<br>b. AACACTGTGAACTGCTTTGTG (SEQ ID NO:67)<br>c. CAACACTGTGAACTGCTTTGT (SEQ ID NO:68) |
| | Trp44Ser | a. GGAGGTGTCGGGAGATGAGCA (SEQ ID NO:69)<br>b. AGGAGGTGTCGGGAGATGAGC (SEQ ID NO:70)<br>c. AAGGAGGTGTCGGGAGATGAG (SEQ ID NO:71) |
| GJB6 | Thr5Met | a. TTGGGGATGCTGCACACTTT (SEQ ID NO:72)<br>b. ATTGGGGATGCTGCACACTT (SEQ ID NO:73)<br>c. GATTGGGGATGCTGCACACT (SEQ ID NO:74) |
| DFNA5 | INV/DEL, Ex8del | a. GAACCAGTGAAATGCCAGATA (SEQ ID NO:75)<br>b. GGAACCAGTGAAATGCCAGAT (SEQ ID NO:76)<br>c. TGGAACCAGTGAAATGCCAGA (SEQ ID NO:77) |
| | 3-bp del 372CTT | a. GAACCAGTGAAATGCCAGATA (SEQ ID NO:78)<br>b. GGAACCAGTGAAATGCCAGAT (SEQ ID NO:79)<br>c. TGGAACCAGTGAAATGCCAGA (SEQ ID NO:80) |
| | IVS7, G > G, −6 | a. GAACCAGTGAAATGCCAGATA (SEQ ID NO:81)<br>b. GGAACCAGTGAAATGCCAGAT (SEQ ID NO:82)<br>c. TGGAACCAGTGAAATGCCAGA (SEQ ID NO:83) |

F. Therapeutic Uses of siRNA Molecules

According to the methods of the invention, the expression of a gene involved in deafness caused by dominant negative mechanism of action can be reduced by introducing a therapeutic nucleic acid molecule of the invention into a cell. For example, the expression of GJB2 can be reduced in a round window membrane cell. A reduction in expression of GJB2 can be due to a reduction in the amount of GJB2 mRNA and/or the encoded polypeptide, and is reduced compared to expression in the absence of the nucleic acid molecule. The term "reduced" is used herein to indicate that expression of GJB2 is reduced by 1-100% (e.g., 10%, 20%, 30%, 40%, 50%, 60%, 70%, 80%, 90%, 95%, or 99% reduced). "Knockdown" or "knock-down technology" refers to techniques in which the expression of a target nucleic acid is reduced compared to expression of the target nucleic acid in the absence of a RNA molecule.

For example, the expression of GJB2 mRNA can be reduced in a cell by antisense, RNAi, or siRNA. A siRNA can be two separate RNA molecules that hybridize together, or a single molecule that forms a hairpin.

The GJB2 nucleic acid molecules of the invention can be used to reduce the expression of GJB2 in a number of cell types or tissue types. For example, the GJB2 nucleic acid molecules of the invention can be used to reduce the expression of GJB2 in round window membrane cells. The nucleic acid molecules of the invention are preferably administered so as to result in an inhibition of GJB2. Inhibition of GJB2 as used herein refers to a decrease in the quantity of GJB2 over a given period of time (e.g., hours, days, weeks, or months).

The amount of a nucleic acid molecule administered will vary depending on various factors including, but not limited to, the composition chosen, the weight, the physical condition, and the age of the individual, and whether prevention or treatment is to be achieved. Such factors can be readily determined by a clinician using animal models or other test systems that are well known in the art. The nucleic acids of the present invention can be delivered to a cell in a number of ways. For example, a nucleic acid molecule of the invention (e.g., a siRNA) can be directly administered to a cell, or a vector encoding a nucleic acid molecule of the invention (e.g., a viral vector) can be administered to a cell. Viral vectors include, without limitation, a lentivirus, an adenovirus, an adeno-associated virus, a retrovirus, a vaccinia virus, a herpes viruses, and a bovine papilloma virus. In addition, a nucleic acid molecule of the invention or a vector encoding such a nucleic acid can be encapsulated in, for example, a nanoparticle or a liposome, and administered to a cell.

A pharmaceutical composition of the invention is formulated to be compatible with its intended route of administration. For example, the therapeutic agent may be introduced directly into the cancer of interest via direct injection. Additionally, examples of routes of administration include parenteral, e.g., intravenous, intradermal, subcutaneous, oral (e.g., ingestion or inhalation), transdermal (topical), transmucosal, and rectal administration. siRNA molecules of the invention can be incorporated into pharmaceutical compositions suitable for administration. Such compositions typically comprise the nucleic acid molecule, and a pharmaceutically acceptable carrier. As used herein, "pharmaceutically acceptable carrier" is intended to include any and all solvents, dispersion media, coatings, antibacterial and anti-fungal agents, isotonic and absorption delaying agents, and the like, compatible with pharmaceutical administration. The use of such media and agents for pharmaceutically active substances is well known in the art.

Solutions or suspensions can include the following components: a sterile diluent such as water for injection, saline solution (e.g., phosphate buffered saline (PBS)), fixed oils, a polyol (for example, glycerol, propylene glycol, and liquid polyetheylene glycol, and the like), glycerine, or other synthetic solvents; antibacterial and antifungal agents such as parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol or sorbitol, and sodium chloride in the composition. Prolonged administration of the injectable compositions can be brought about by including an agent that delays absorption. Such agents include, for example, aluminum monostearate and gelatin. The parenteral preparation can be enclosed in ampules, disposable syringes, or multiple dose vials made of glass or plastic.

In one embodiment, the therapeutic composition (e.g., plasmid and/or siRNA-liposome complex) can be placed directly on the round window membrane. For example, a small piece of Gelfoam® absorbable gelatin sponge soaked with the lipocomplex is inserted in the round window niche using a microsyringe equipped with a fine polyimide cannula and placed in direct contact with the round window membrane. The round window niche may be partially or entirely covered with the Gelfoam® absorbable gelatin sponge.

It is especially advantageous to formulate compositions in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the invention are dependent upon the amount of a compound necessary to inhibit proliferation of the cancer cells. The amount of a compound necessary to inhibit proliferation of the cancer cells can be formulated in a single dose, or can be formulated in multiple dosage units. Treatment may require a one-time dose, or may require repeated doses.

G. Articles of Manufacture

The invention encompasses articles of manufacture (e.g., kits) that contain one or more nucleic acid molecules of the invention, or one or more vectors that encode a nucleic acid molecule of the invention. Such nucleic acid molecules are formulated for administration as described herein, and are packaged appropriately for the intended route of administration. For example, a nucleic acid molecule of the invention or a vector encoding a nucleic acid molecule of the invention can be contained within a pharmaceutically acceptable carrier.

Kits of the invention also can include additional reagents (e.g., buffers, co-factors, or enzymes). Pharmaceutical compositions of the invention further can include instructions for administering the composition to an individual. The kit also can contain a control sample or a series of control samples that can be assayed and compared to the biological sample. Each component of the kit is usually enclosed within an individual container and all of the various containers are within a single package.

H. Administration of Nucleic Acid Molecules

The invention features a pharmaceutical composition comprising one or more nucleic acid(s) of the invention in an acceptable carrier, such as a stabilizer, buffer, and the like. The polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration, suppositories for rectal administration, sterile solutions, suspensions for injectable administration, and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or subject, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes exposes the NA molecules of the invention to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful By "pharmaceutically acceptable formulation" is meant a composition or formulation that allows for the effective distribution of the nucleic acid molecules of the instant invention in the physical location most suitable for their desired activity. Non-limiting examples of agents suitable for formulation with the nucleic acid molecules of the instant invention include: P-glycoprotein inhibitors (such as Pluronic P85), which can enhance entry of drugs into the CNS (Jolliet-Riant and Tillement, 1999, Fundam. Clin. Pharmacol., 13, 16-26); biodegradable polymers, such as poly (DL-lactide-coglycolide) microspheres for sustained release delivery after intracerebral implantation (Emerich, D F et al, 1999, Cell Transplant, 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (Schroeder et al., Prog Neuropsychopharmacol Biol Psychiatry, 23, 941-949, 1999). Other non-limiting examples of delivery strategies for the nucleic acid molecules of the instant invention include material described in Boado et al., 1998, J. Pharm. Sci., 87, 1308-1315; Tyler et al., 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058.

The invention also features the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated by reference herein. For example, preservatives, stabilizers, dyes and flavoring agents can be provided. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered.

The nucleic acid molecules of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative, and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

The invention will be further described in the following examples, which do not limit the scope of the invention described in the claims.

EXAMPLES

Example 1

Suppression of GJB2 Expression by RNA Interference

One gene of particular relevance in the field of auditory science is GJB2. Its single coding exon (exon 2) encodes a 26 kD isoform of the transmembrane protein family of connexins called Connexin 26 (CX26). Connexins oligomerize to form hexameric units called connexons, the constituent components of gap junctions.

In the murine cochlea, Gjb2 gap junctions are hypothesized to facilitate potassium recycling in the inner ear. After entry into hair cells during mechanosensory transduction, potassium is released by basolaterally expressed KCNQ4 potassium channels and taken up by adjacent supporting cells. These cells are interconnected by Gjb2 gap junctions to form the epithelial gap junction pathway, which shunts potassium to the lower part of the spiral ligament. Potassium then passes through a connective tissue pathway of fibrocytes functionally linked by Gjb2 gap junctions to the stria vascularis and ultimately into the scala media.

GJB2 allele variants are found in half of persons with congenital severe-to-profound autosomal recessive non-syndromic hearing loss (ARNSHL), making mutations in this gene the most common cause of recessive genetic deafness in many world populations (Kelsell, D. P. et al. *Nature* 387, 80-83 (1997); Denoyelle, F. et al. *Hum. Mol. Genet.* 6, 2173-2177. (1997); Estivill, X. et al. *Lancet.* 351, 394-398 (1998); Green, G. E. et al. *JAMA.* 281, 2211-2216 (1999)). Three particularly common deletions in the open reading frame of GJB2, namely 35delG, 167delT and 235delC, lead to premature protein termination in northern European and Mediterranean, Ashkenazi Jewish and Japanese populations, with mutation specific carrier frequencies ranging from 1% to 4%.

A few mutant alleles of GJB2 also cause autosomal dominant non-syndromic hearing loss (ADNSHL) through a dominant-negative effect (Denoyelle, F et al. *Nature.* 393, 319-320 (1998); Janecke, A. R. et al. *Hum. Genet.* 108, 269-270 (2001)). The incidence of these allele variants is low and the associated deafness is commonly syndromic, as it segregates with various types of skin disorders. Among the dominant mutations, which include W44C, R75W and D66H, R75W is a well-characterized cause of deafness and palmoplantar keratoderma (Richard, G. et al. *Hum. Genet.* 103, 393-399 (1998)). R75W connexons inhibit intercellular coupling of paired *Xenopus* oocytes co-injected with wildtype GJB2 or GJA1 (Rouan, F. et al., *J. Cell Sci.* 114, 2105-2113 (2001)), and the dye-transfer capacity of GJB6-heteromeric connexons in Hela cells (Marziano, N. K. et al., *Hum. Mol. Genet.* 12, 805-812 (2003)).

The present inventors transfected cochleae of adult mice with a plasmid vector expressing GJB2$_{R75W}$-eGFP (Di, W. L. et al., *Cell Commun. Adhes.* 8 415-418 (2001).

Results

In Vitro Suppression of GJB2 Expression

The inventors conducted initial RNAi experiments measuring endogenous expression of either GJB2 or Gjb2 in human HEK293 and mouse P19 cells, respectively, to identify potent duplexes that selectively suppress human GJB2 expression. Four siRNA-targeting sites of sequence type AA(N19) (N, any nucleotide) were selected from the coding region of human GJB2 mRNA (siRNA 1-4) according to published guidelines (FIG. 1) (Elbashir, S. M. et al., *EMBO J.* 20, 6877-6888 (2001); Wadhwa, R. et al., *Mutat. Res.* 567, 71-84 (2004)). siRNA2m was designed as a mouse Gjb2-targeting siRNA homologous to siRNA2.

Synthetic siRNAs were introduced into cultured cells using a polyamine transfection reagent (siPORT™ Amine, Ambion, Inc). Cy3-labeled siRNA1 and biotin-labeled siRNA2m were clearly detected in the cytoplasm of transfected cells, with transfection efficiencies of 90.3±3.1% (HEK293 cells, mean±sd) and 78.6±3.6% (P19 cells, mean±sd). Reverse transcription polymerase chain reaction (RT-PCR) analysis showed that siRNA1 specifically suppressed GJB2 mRNA in HEK293 cells, as assessed by comparison with scrambled-sequence siRNAs or transfection reagent only. A GAPDH-targeting siRNA that successfully induced GAPDH mRNA suppression did not affect GJB2 expression, and siRNA1 exerted no remarkable effect on GAPDH expression.

To quantitate GJB2 suppression by GJB2-targeting siRNAs, RT-PCR of endogenous GJB2 expression was quantified by densitometry and expressed as a band intensity value (BIV). Log [BIVs] of GJB2 expression correlated linearly with the number of amplification cycles in the exponential ranges of 28-34 (r=0.961, p<0.01; n=7), using 100 ng total RNA per PCR. When 12.5, 25, 50, 75, 100, 150 or 200 ng of RNA was used in RT per each PCR with GJB2 primers and 30 thermocycles, BIVs correlated with the amount of RNA added per PCR (r=0.808; p<0.001; n=6, for each RNA amount). Therefore, BIVs of GJB2 were determined in each sample following 30 thermocycles using 100 ng of total RNA per PCR. Levels of gene transcription were compared to GJB2 expression in control samples prepared with negative control siRNAs and expressed as percentage relative abundance (RA) of mRNA.

GJB2 expression was suppressed by more than 80% of control levels by siRNA2 (15.9±11.1%, mean±sd.; n=7; p<0.01), and by approximately 50% of control levels by siRNA1 (48.2±11.8%; n=7; p<0.01) and siRNA3 (59.1±18.1%; n=7; p<0.01) at 72 h post transfection; siRNA4 was ineffective at the same time point (69.4±30.1%; n=7; p=0.116) (FIG. 2A). Suppression of GJB2 mRNA by siRNA2 was demonstrated at 48 h (19.7±12.3%; n=6; p<0.05), 72 h (15.9±11.1%; n=6; p<0.001) and 120 h (53.6±14.4%; n=6; p<0.05) post transfection, but reversed to control levels by 168 h (125.2±32.3%; n=6; p=0.337) post transfection in HEK293 cells (FIG. 2B). At 72 h post transfection (maximum GJB2 suppression), siRNA2 induced no significant change in the expression of GJB3 (73.9±28.5%; n=7; p=0.116) or GJA1 (79.9±28.5%; n=16; p=0.228) (FIG. 2C). GJB6 is not expressed constitutively in HEK293 cells and remained undetectable in the presence of siRNA2 reduction.

In accordance with the suppression of human GJB2 by siRNA2, siRNA2m induced significant reduction in endogenous Gjb2 expression in mouse P19 cells as compared to negative control siRNAs (37.3±31.5%, n=7 vs. 100.0±32.8%, n=7; p<0.05). siRNA4, with complete sequence identity between human and mouse, exerted no significant effect on Gjb2 expression levels (69.9±24.8%, n=7; p=0.142) (FIG. 3).

As a prerequisite step to studying the effect of RNAi in vivo, a CMV-driven mammalian expression vector conferring human GJB2$_{R75W}$-eGFP (pGJB2$_{R75W}$-eGFP) was introduced in mouse P19 cells using a cationic liposome reagent (Lipofectamine™2000, Invitrogen, Corp). pGJB2$_{R75W}$-eGFP was derived originally from the expression plasmid pEGFP-N1 (Clontech, BD Biosciences, Inc.) (Di, W. L. et al., Cell Commun. Adhes. 8 415-418 (2001)). Co-transfection with siRNA2 or negative control siRNA confirmed efficient and specific silencing of GJB2$_{R75W}$-eGFP expression. siRNA2 reduced transgene mRNA to less than 20% of levels seen using negative control siRNAs, (11.0±4.3%, n=7 vs. 100.0±24.8%, n=7; p<0.01), abolishing GJB2$_{R75W}$-eGFP fluorescence. Endogenous Gjb2 mRNA was co-suppressed by siRNA2 but remained at approximately 60% of control levels in cell cultures (60.3±14.7%, n=7; p<0.05).

In Vivo GJB2R75W-eGFP Transgene Expression

In vivo transfection of the mutant GJB2$_{R75W}$-eGFP into adult mouse cochleae was achieved by complexing pGJB2$_{R75W}$-eGFP (25 µg/100 µl of lipocomplex solution) with 4 mM DOTAP:cholesterol cationic liposome (Templeton, N. S. et al. Nat. Biotechnol. 15, 647-652 (1997)), following the manufacturer's protocol (In vivo GeneSHUTTLE™, Qbiogene, Inc), and applying 1-2 µl of the lipocomplex to a small piece of Gelfoam® absorbable gelatin sponge, which was placed against the intact round window membrane. Exposure to the round window membrane was obtained through an anterior cervical approach to the middle ear (Jero, J. et al. Hum. Gene Ther. 12, 539-548 (2001)), a relatively atraumatic procedure that permits post-operative assessment of hearing.

RT-PCR demonstrated GJB2$_{R75W}$-eGFP mRNA expression in the operated ear 72 h after surgery. Transgene expression was not detectable in the contralateral ear or in control ears with vehicle-only application. Immunohistochemistry using an anti-eGFP monoclonal antibody (BD Biosciences, Inc.) showed pronounced expression in the epithelial cells of the basal membrane, inner and outer pillar cells, outer hair cells, and in the spiral limbus and spiral ligament.

Click-ABR thresholds in the operated and contralateral ears were determined at the same time point, using incremental steps of 5 dB from 0-100 sound pressure level (SPL) in a sound-proof booth as described previously (McGuirt, W. T. et al. Nat. Genet. 23, 413-419 (1999)). Hearing impairment was measured as a change in the intraaural differences of ABR thresholds for each mouse. pGJB2$_{R75W}$-eGFP (25 µg/100 µl) induced a significant increase in ABR thresholds compared to lipocomplexes with empty vector (25 µg/100 µl) (20.0±10.4 dB, n=8 vs. 8.8±5.8 dB, n=8; p<0.05) or vehicle-only application (5.6±3.2 dB, n=8; p<0.01). There was no significant difference in hearing between empty vector and vehicle-only control animals (p=0.194) (FIG. 4).

Suppression of GJB2$_{R75W}$-eGFP Expression and its Effect on Phenotype

In-vivo RNAi was assessed in 4 study groups using liposome complexes composed of (1) 25 µg pGJB2$_{R75W}$-eGFP; (2) 25 µg pGJB2$_{R75W}$-eGFP plus 25 µg empty vector; (3) 25 µg pGJB2$_{R75W}$-eGFP plus 25 µg negative control siRNAs; and, (4) 25 µg pGJB2$_{R75W}$-eGFP plus 25 µg GJB2-targeting siRNA2, all in 100 µl of DOTAP:cholesterol lipocomplex.

Figure 1:
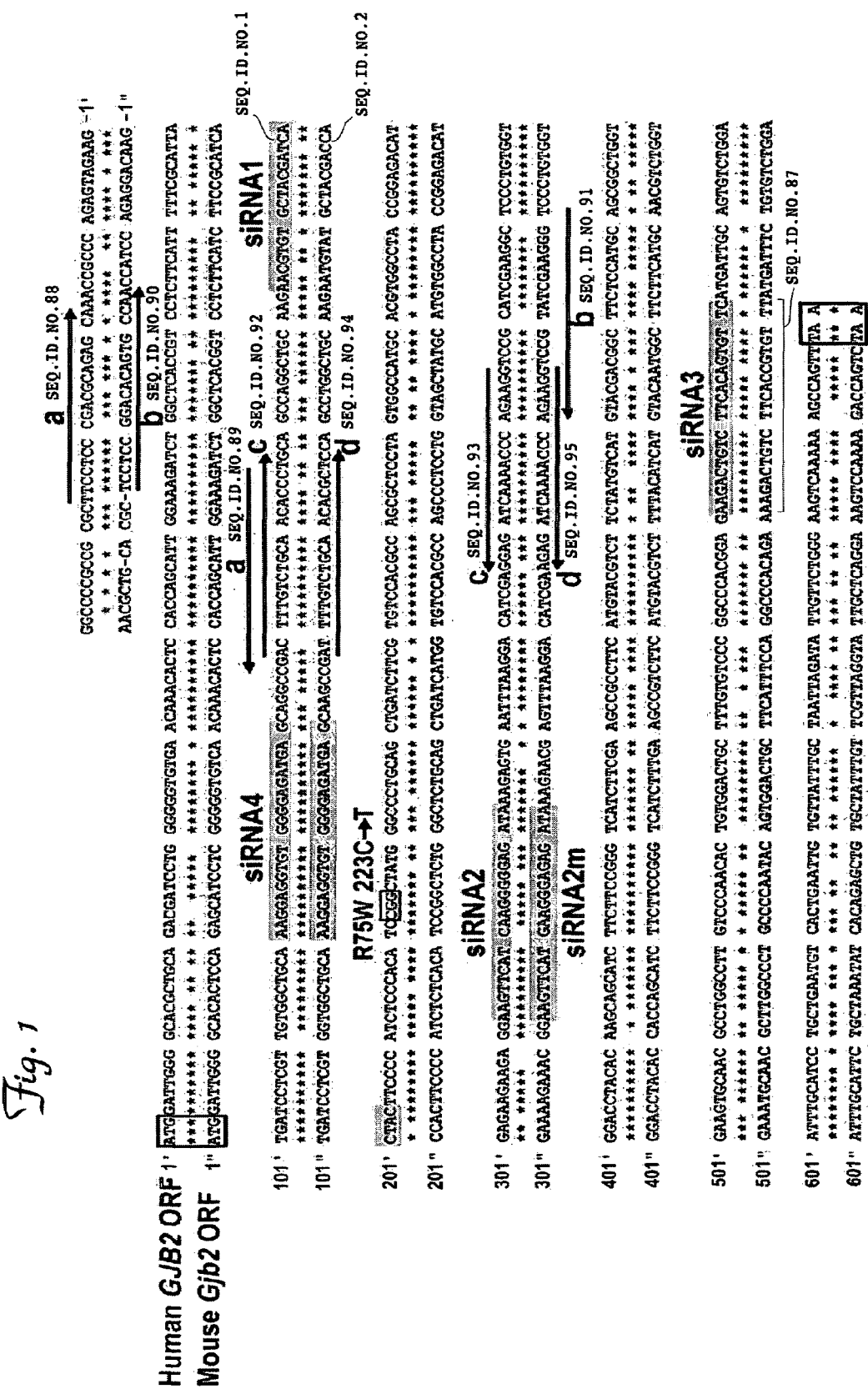
FIG. 1. siRNA targeting sites designed within the ORF of human GJB2 (SEQ ID NO:7) and mouse Gjb2 (SEQ ID NO:8) (shaded sites, siRNA1-4, siRNA2m and siRNA4m). Primer pairs (a, SEQ ID NO:88 and SEQ ID NO:89) and (b, SEQ ID NO:90 and SEQ ID NO:91) were used to amplify endogenous GJB2 (HEK293 cells) and Gjb2 (P19cells), respectively, by RT-PCR. Primer pairs (c, SEQ ID NO:92 and SEQ ID NO:93) and (d, SEQ ID NO:94 and SEQ ID NO:95) are specific for human GJB2 (GJB2$_{R75W}$ transgene) and mouse Gjb2 mRNA. R75W and the initiation and termination codons are indicated by boxes. The multicloning site of pGJB2$_{R75W}$-eGFP contains the ORF but not the untranslated regions of GJB2$_{R75W}$.

Semiquantitative RT-PCR analysis was performed with specific primers for human or mouse GJB2/Gjb2 (primer pairs c and d in FIG. 1). Typically 10-20 ng RNA was PCR amplified in the exponential phase, measuring Gapdh levels as an internal control and expressing mRNA levels as percentage RA. Gjb2 amplification correlated with the amount of RNA added per PCR (range of RNA, 7-56 ng; r=0.944; n=36; p<0.0001).

Among groups 1, 2 and 3, in cochlear tissues dissected at 72 h post treatment, levels of GJB2$_{R75W}$-eGFP mRNA in group 1 (138.3±28.7%, n=6) were higher than in groups 2 (85.8±29.8%, n=6; p<0.05) and 3 (100.0±11.5%, n=6; p<0.05), although differences between groups 2 and 3 were not significantly different (p=0.525). It is likely that the total amount of nucleic acid in group 1 affected the formulation of the lipocomplex (Templeton, N. S. et al. Improved DNA: liposome complexes for increased systemic delivery and gene expression. Nat. Biotechnol. 15, 647-652 (1997)), resulting in a difference in in vivo transfection.

In group 4, siRNA2 significantly reduced GJB2$_{R75W}$-eGFP mRNA to less than 30% of levels in group 3 (27.6±2.6%, n=6 vs. 100.0±10.6%, n=6; p<0.01), but did not affect levels of endogenous Gjb2 mRNA (116.1±15.6%, n=6) as compared to either group 2 (113.4±34.9%, n=6) or group 3 (100±21.0%, n=6; p=0.523). The hearing loss seen with GJB2$_{R75W}$-eGFP expression was prevented by siRNA2—intraaural differences in ABR thresholds in group 4 (15.0±12.5 dB, n=10) were significantly lower than in group 3 (23.0±8.6 dB, n=10; p<0.05), and were not statistically different from the control animals with empty vector only (p=0.287) (FIG. 4).

Discussion

The inventors have shown that siRNAs can be used to suppress human GJB2 expression in vitro and in vivo. The most potent siRNA tested selectively suppressed by more than 70% mutant GJB2$_{R75W}$-eGFP expression in murine cochleae without significantly decreasing expression of endogenous Gjb2. Suppression of GJB2$_{R75W}$-eGFP expression by siRNA2 prevented hearing loss otherwise associated with the R75W dominant-negative allele variant of CX26.

The major post-transcriptional mechanism of eukaryotic RNAi involves incorporation of siRNAs into RISC. The sequence-specific endonuclease activity of RISC can be reconstituted in cytosolic extracts of Hela cell (Martinez, J. et al., Cell 110, 563-574 (2002)). The inventors have shown that in mammalian cultured cells, select chemically synthesized siRNAs localize in the cytoplasm and specifically deplete GJB2 mRNAs. siRNA2 was identified as the most potent of four GJB2-targeting siRNAs tested in this study: siRNA2 depleted expression of both endogenous GJB2 and plasmid-delivered GJB2$_{R75W}$-eGFP to less than 20% of control levels in cultured cells. GJB2$_{R75W}$-eGFP fluorescence was abolished by siRNA2.

The 21-nt sequence of siRNA2 shares a 12-nt match in maximum alignment with GJB3 and GJA1 mRNA, the two other connexin isoforms expressed in this cell line, but expression levels of these connexins did not change. siRNA2 also has sequence mismatches against mouse Gjb2 mRNA at the $9^{th}$ and $15^{th}$ nucleotide positions in its 21-nt target sequence. These 2-nt mismatches were sufficient to distinguish human GJB2$_{R75W}$-eGFP and endogenous murine Gjb2 alleles in vivo, with selective depletion of GJB2$_{R75W}$-eGFP mRNA to less than 30% of control levels, while maintaining endogenous Gjb2 expression.

GJB2$_{R75W}$-eGFP inhibits function of wild-type Gjb2 and permeability of gap junction hemichannels in vitro and causes hearing loss in vivo. siRNA2 was potent enough to modify the phenotype caused by expression GJB2$_{R75W}$-eGFP, decreasing the expected ABR threshold shift. This observation raises the possibility of allele-specific RNAi as a therapeutic option to mitigate some types of sensorineural deafness caused by dominant negative mechanisms.

As a therapeutic option for this type of deafness, RNAi must be potent enough to prevent the expression of the mutant allele but permissive enough to preserve expression of the wild type transcript at levels sufficient to permit normal inner ear function. It is possible to rescue a deafness phenotype by means of allele-specific RNAi targeting mutant GJB2 alleles. Haploinsufficiency of GJB2 does not cause hearing loss in humans, and in mouse mutants heterozygous for a targeted deletion of Gjb2 (Gjb2+/−) hearing loss does not develop despite wild-type Gjb2 mRNA level that are 50% of normal (46.5±20.0%, n=6 vs. 100.0±17.6%, n=6).

The inventors focused specifically on the application of lipocomplexes to the round window membrane, as this approach can be performed easily on humans and does not require opening the inner ear, thus minimizing the possibility of iatrogenic damage to the cochlea. The inventors applied lipocomplexed plasmid and/or siRNAs on the intact RWM, and successfully detected transgene expression in cochlea by RT-PCR and immunohistochemistry. It is reasonable to assume the lipocomplexes diffused through the RWM into the scala tympani and through the porous osseous spiral lamina into the basal epithelial cells in the organ of Corti (Duckert, L. G. & Duvall, A. J. III. *Otolaryngology*. 86, 434-446 (1978); Shepherd, R. K. & Colreavy, M. P. *Arch. Otolaryngol. Head Neck Surg.* 130, 518-523 (2004)). These cells are part of the CX26 functional syncytium, and although preserved residual hearing suggests that the gap junction system was not completely disrupted by expression of $GJB2_{R75W}$-eGFP, hearing thresholds were increased and this increase was prevented by concomitant transfection with siRNAs.

Methods siRNA Preparation

Target sequences of siRNAs 1, 2, 3 and 4 respectively correspond to c.c. 184-204, 313-333, 562-582 and 120-140 of human GJB2; siRNA2m and siRNA4m correspond to c.c. 313-333 and 120-140 of mouse Gjb2. Since siRNA4 and siRNA4m are identical, only the designation siRNA4 is used. Specificity was tested using the BLAST search engine on the world-wide-web (ncbi.nlm.nih.gov/BLAST) and excluding orthologous identity, no siRNA had matches of more than 13 nt to known human or murine mRNAs or expressed sequence tags (ESTs). siRNA targeting GAPDH, and scrambled siRNA without significant homology to known human and murine genes (negative control siRNAs) were obtained from Ambion, Inc. siRNA with the same nucleotide composition as siRNA2 but without significant homology to known genes was designed as a negative control for experiments with siRNA2 (siRNA Scrambler, on the world-wide-web at genscript.com/ssl-bin/app/scramble, GenScript Corp).

RNAs were chemically synthesized and PAGE purified by Ambion, Inc. 2'-deoxythymide residues were used as the 3' overhangs in the both sense and antisense strands so that 19 nt-RNA duplexes with symmetric 2-nt overhangs were formed. Twenty 1M amounts of sense and antisense RNAs were heated at 90° C. in 50 µl of annealing buffer (Ambion, Inc) for 1 m and annealed at 37° C. for 60 m; aliquots were stored at −20° C. Fluorescence-labeling of siRNA1 and negative control siRNA was performed using a Cy3-siRNA labeling kit (Ambion, Inc). The 3' ends of both strands of siRNA2m were biotinylated and PAGE purified by Dharmacon, Inc. Annealing and labeling of siRNAs were verified by 20% PAGE.

Cell Culture and Transfection

Human HEK293 cells and mouse P19 cells were maintained respectively in Dulbecco's modified Eagle's medium (DMEM) (Gibco Cell Culture Systems, Invitrogen Corp) with 10% fetal bovine serum (FBS) (HyClone Corp) and α-Minimum Essential Medium (Gibco Cell Culture Systems, Invitrogen Corp) with 7.5% bovine calf serum (HyClone Corp) plus 2.5% FBS, in a humidified incubator at 37° C. and 5% $CO_2$ and regularly passaged at sub-confluence. Twenty-four hours before transfection, cultured cells were trypsinized, diluted in fresh medium without antibiotics (HEK293 cells, $5.0 \times 10^6$ cells $ml^{-1}$; P19 cells, $4.0 \times 10^5$ cells $ml^{-1}$) and transferred to 12-well plates (400 ul per well). Cell confluency was 50-70% at the time of transfection.

siRNA transfection of HEK293 cells was carried out with siPORT™ Amine transfection reagent (Ambion, Inc) using 100 nM siRNA duplex (1.33 µg/ml) in a final volume of 500 µl per well. Growth media (2.5 ml/well) was added 12 h later and cells were harvested 72 h post transfection. For P19 cells, transfection was carried out in opti-MEM1 reduced serum medium (Gibco Cell Culture Systems, Invitrogen Corp) with siPORT™ Amine using 200 nM siRNA (2.66 µg/ml); growth media was added 12 h later and cells were harvested at 42 h post transfection. $pGJB2_{R75W}$-eGFP was provided by Professor David Kelsell (Centre for Cutaneous Research, London) (Di, W. L. et al., *Cell Commun. Adhes.* 8 415-418 (2001)). $pGJB2_{R75W}$-eGFP (1.3 µg/ml) and 200 µM GJB2-targeting siRNA (GJB2siRNA2) or 200 µM negative control siRNA were introduced to mouse P19 cells using Lipofectamine™ 2000 (Invitrogen, Corp). Co-transfection was performed at a cell confluency of $1.5 \times 10^5$ cells $ml^{-1}$ and final transfection volume of 1.2 ml.

RNA Extraction and Reverse Transcription

Cultured cells were lysed in a buffer containing β-mercaptoethanol, processed for RNA extraction using an RNeasy® column (Qiagen, Inc) and treated with DNaseI (Qiagen, Inc). Amounts of RNA were quantitated by measuring absorbency at 260/280 nm; usually 3.5-5 µg and 2-3.5 µg of total RNA were purified from each well of HEK293 and P19 cells, respectively. Typically, 500 ng of total RNA (10 ng per RT-PCR) was subjected to reverse transcription in a 20 µl reaction mixture containing reaction buffer, 0.5 mM of each dNTP, 1 µM oligo dT primers, 20 units RNase inhibitor and 200 units MMLV reverse transcriptase, according to the manufacturer (Advantage® RT-for-PCR kit, Clontech, Inc.). Four µl of the RT mixture was added to a 50 µl PCR mixture.

For RNA purification from mouse cochleae, the animals were euthanized with $CO_2$, blood was removed by transcardiac perfusion of PBS, and cochlear tissue was dissected and frozen in liquid nitrogen. The tissue was homogenized in the same buffer and subjected to total RNA extraction and DNaseI treatment. 240-480 ng of total RNA was usually obtained from 6 cochleae, 100-200 ng RNA (10-20 ng per RT-PCR) was used for RT in a 20 µl reaction mixture, and 2 µl of RT mixture was added per PCR.

PCR and Data Analysis

Primer pairs for GJB2 (FIG. 1: primer pair a, c.c. −37 to −19, sense (SEQ ID NO:88); c.c. 147 to 166, antisense (SEQ ID NO:89)), GJA1 (c.c. −24 to −5; c.c. 165 to 185), GJB3 (c.c. 104 to 123; c.c. 392 to 411) and GJB6 (c.c. −30 to −11; 163 to 183) respectively amplified 203, 209, 308 and 213-bp fragments of human connexin cDNAs; human GAPDH primers (c.c. −21 to −3; c.c. 159 to 178) amplified a 199-bp fragment. Primers for mouse Gjb2 (FIG. 1: primer pair b, c.c. −36 to −17 (SEQ ID NO:90); c.c. 371 to 391 (SEQ ID NO:91)) and Gapdh (c.c. 650 to 669; c.c. 976 to 995) amplified 427 and 346-bp fragments of murine cDNAs. Specific primers for human GJB2 (FIG. 1: primer pair c, c.c. 149 to 168 (SEQ ID NO:92); c.c. 357 to 376 (SEQ ID NO:93)) and mouse Gjb2 (FIG. 1: primer pair d, c.c. 149 to 168 (SEQ ID NO:94); c.c. 357 to 376 (SEQ ID NO:95)) were designed utilizing interspecies difference at the 3' ends of both primers and used to amplify 228-bp products from cochlear tissue of mice.

Each PCR reaction mixture (50 ul) contained the reaction buffer, 1.5 mM MgCl2, 0.2 mM of each dNTP, 0.5 µM each of the appropriate primers, 2.5 U DNA polymerase (Bioline USA Inc, Randolph, Mass.) and RT reaction mix. 19-37 cycles of PCR amplification of human cDNA were completed at 94° C. for 30 s, 60° C. for 30 s and 72° C. for 30 s in a GeneMate® Genius PCR machine (ISC BioExpress, Inc). For amplification of cDNA from cochlear tissue, PCR was performed at 95° C. for 9 m followed by 27-45 cycles of 94° C. for 30 s and 60° C. for 30 s in a reaction mix that contained the previously listed ingredients, substituting AmpliTaq® Gold DNA polymerase (Applied Biosystems, Inc) for DNA polymerase.

For semiquantitative RT-PCR, EtBr-stained PCR products were resolved on 3% agarose gels, imaged using a CCD camera (RT-Slider, Diagnostic Instruments, Inc) and quantified by densitometry using GelExpert™ software (Nucleovision, Nucleotech, Inc). After subtraction of background values as determined in an adjacent band-free area, the signal intensity was expressed as BIV. Differences between groups were examined non-parametrically using the Kruskal-Wallis test and Mann-Whitney U-test. Statistical significance was assigned to P-values of <0.05.

Fluorescence Microscopy

HEK293 cells were grown on coverslips in 12-well plates. Transfection with the Cy3-labeled siRNA was performed under the same conditions as described for siRNA transfection. After incubation for 72 h, cells were washed in DMEM without serum and incubated in 5% $CO_2$ with 5 µM chloromethylfluorescein diacetate in DMEM for 45 at 37° C., and then maintained in DMEM with 10% FBS for 30 m at 37° C., in order to allow the cytosolic esterase and glutathione transferase to transform the chloromethylfluorescein to a cell impermeant-fluorescent dye to visual the cytoplasm of living cells (Cell Tracker™, Molecular Probes, Inc). After washing in PBS, cells were fixed with 4% formaldehyde in PBS for 15 m. Coverslips were washed in PBS, mounted in Vectashield medium with DAPI (Vector Laboratories, Inc) and examined by fluorescence microscopy (BX-51, Olympus, Inc). Data were recorded with a CCD camera (RT-Slider, Diagnostic Instruments, Inc) and processed by image analysis software (SPOT software, Diagnostic Instruments; Photoshop, Adobe Systems, Inc).

Transfection efficiency was determined in HEK293 and P19 cells 12 h after transfection by counting the number of cells with Cy3-siRNA signal and the total number of cells in the microscopic field; this process was repeated three times. Biotin-labeled siRNA2m was tested for transfection and localization in P19 cells. Cells transfected by biotin-siRNA2m were washed in PBS, fixed with 4% formaldehyde for 7 m, incubated with a peroxidase block reagent (DAKO) for 5 m, and permeabilized by 0.1% TritonX-100 in PBS for 7 m. The biotinylated siRNA was visualized by the ABC-DAB method (Vectastain® ABC kit, Vector Laboratories, Inc).

Animal Model

Female C57B16 mice (postnatal day 42-45) were anesthetized with intraperitoneal ketamine (100 mg/kg) and xylazine (9 mg/kg). Procedures were performed on the right ear via a ventral, paramedian incision in the neck. A small opening in tympanic bulla was made to provide direct visualization of the round window membrane, as described by Jero et al. (*Hum. Gene Ther.* 12, 539-548 (2001)). 1-5 microliter volume of the plasmid and/or siRNA-liposome complex was placed in the round window niche using a microsyringe equipped with a fine polyimide cannula (I.D.=0.12 mm, O.D.=0.16 mm, MicroLumen, Tampa, Fla., U.S.A.) (Prieskorn, D. M. & Miller, J. M. *Hear. Res.* 140, 212-215 (2000)). Excess solution was gently aspirated and a small piece of Gelfoam® absorbable gelatin sponge soaked with the lipocomplex was placed in direct contact with the round window membrane. For transgene detection by RT-PCR and immunohistochemistry, the round window niche was entirely covered with the Gelfoam® absorbable gelatin sponge. Postoperatively, the incision was sutured and chloramphenicol (30 mg/kg) was administered intramuscularly.

Auditory Brainstem Response Testing

Animals were anesthetized using the same anesthetics and click sounds were unilaterally presented via a microphone inserted into the external auditory canal. Response thresholds were determined by decreasing the stimulus level by 5 dB decrements from 0-100 SPL. The threshold response in the right ear was determined relative to the response in the left ear, to minimize variation between mice. Differences between experimental groups were compared with the Kruskal-Wallis test and Mann-Whitney U-test. Significance was assigned to P-values of <0.05.

Immunohistochemistry

Animals were intracardially perfused with PBS and then 4% formaldehyde. Cochleae were dissected and after making a hole at the apex, immersion fixed at 4° C. for 12 h. They were decalcified in 0.2M EDTA for 48 h, dehydrated through graded alcohol and xylene, and embedded in paraffin. Paraffin sections of 6 µm thickness were dewaxed and incubated with a mouse monoclonal antibody against eGFP (1:200 dilution; BD Biosciences, Inc) at 4° C. overnight. After washing, bound antibody was reacted with Alexa Fluor® 488-anti mouse IgG antibody (Molecular Probes, Inc) for 4° C. for 4 h. Specimens were mounted in Vectashield® medium with DAPI (Vector Laboratories, Inc), and examined by fluorescence microscopy.

Example 2 siRNA-Mediated Post-Transcriptional Silencing of Dominant Negative Alleles of KCNQ4

Hearing loss is the most common sensory defect in humans. At least 60% of congenital and early-onset non-syndromic hearing loss has a Mendelian basis. Autosomal dominant deafness accounts for approximately 15% of inherited hearing loss. To date, 21 genes for dominant deafness have been identified, and a further 33 loci have been mapped to chromosomal regions. In most cases, the genes were mapped and identified following linkage analysis in large families. Mutations in several different genes that cause autosomal dominant deafness lead to a hearing loss phenotype through a dominant-negative mechanism of action (Kubisch C, et al. Cell 1999; 96(3): 437-46; Denoyelle F, et al. Nature 1998; 393(6683): 319-20; Coucke P J, et al. Hum Mol Genet 1999; 8(7): 1321-8). One such example is deafness at the DFNA2 locus, which is caused by mutations in KCNQ4 and is found in many populations (Kubisch C, et al. Cell 1999; 96(3): 437-46; Coucke P J, et al. Hum Mol Genet 1999; 8(7): 1321-8).

KCNQ4 is organized into 14 exons that encode a protein with 6 transmembrane domains and a P-loop to confer $K^+$ ion selectivity to the channel pore (Coucke P J, et al. Hum Mol Genet 1999; 8(7): 1321-8). A voltage sensor in the fourth transmembrane domain drives a conformational change that leads to channel opening. KCNQ4 subunits are typically organized into homotetramers to form functional channels (Coucke P J, et al. Hum Mol Genet 1999; 8(7): 1321-8).

Four of the six known mutations that cause DFNA2 cluster in exons that encode the P-loop: G285S, G285C, L274H and W276S (van Hauwe P, et al. Am J Med Genet 2000; 93(3): 184-7). The G285S allele was the first DFNA2 mutation identified and a mouse model of this variant has been generated (Kharkovets T, et al. EMBO J 2006; 25(3): 642-52. Epub 2006 Jan. 26). The substitution of a serine for a glycine affects the first highly conserved glycine in a GYG signature sequence of the P-loop of the channel pore and abolishes channel function by preventing correct submit assembly. Impaired KCNQ4 function in the inner ear affects $K^+$ ionrecycling.

Normally, mechano-sensory transduction leads to an increase in cytosolic $K^+$ in the outer hair cells of the cochlea, the major site of KCNQ4 expression. KCNQ4 channels expressed in the base of these cells transport $K^+$ extracellularly, where the ion is taken up by supporting cells and cycled back into the scala media (Kubisch C, et al. Cell 1999; 96(3): 437-46). The consequence of abnormal KCNQ4 function is apoptosis of the outer hair cells. The clinical manifestation of this damage is hearing loss that is progressive and biased to the high frequencies (Kubisch C, et al. Cell 1999; 96(3): 437-46).

There is no treatment currently available to prevent or restore hearing in individuals with this dominant-negative form of sensorineural hearing loss. Recently, a process of post-transcriptional gene silencing mediated by double-stranded (ds) RNAs has been described which serves as a conserved cellular defense mechanism for controlling expression of alien genes in protists, filamentous fungi, plants and animals (Fire A. Trends Genet 1999; 15(9): 358-63). It is believed that generation of dsRNAs is triggered by random integration of alien genes and leads to degradation of homologous single-stranded mRNA. The process of RNA interference (RNAi) has rapidly become an important tool for reverse genetic studies targeting mammalian genes (Elbashir S M, et al. EMBO J 2001; 20(23): 6877-88). In a recent proof-of-principle study, RNAi technology was shown to protect against hearing loss caused by the dominant-negative expression of a GJB2 (connexin 26) allele (Example 1 above). A short interfering RNA (siRNA) was identified that potently suppressed post-transcriptional expression of the R75W allele of GJB2 in a mammalian cell line and mouse model. This powerful new technology is applied to dominant-negative alleles of KCNQ4 to prevent DFNA2 hearing loss.

The present experiment involves: 1) post-transcriptional silencing of allele variants of the KCNQ4 gene that cause hearing loss using RNAi technology and, 2) identification of a human autosomal dominant hearing loss gene. Small interfering RNAs (siRNAs) are specifically designed to four alleles of KCNQ4. The ability of the siRNAs to knockdown expression of the mutant G285S allele of KCNQ4 is assessed on cell lines and a mouse model in a proof-of-principle study. The causative gene in a family with autosomal dominant deafness is identified using a SNP genotyping approach.

Materials and Methods

Animal Resources: Human KCNQ4 and its murine orthologue show 96% sequence identity and 97% sequence similarity. The studies are performed using murine Kcnq4 because a mouse mutant expressing the murine equivalent of the G285S allele (murine G286S) has been made that faithfully recapitulates the human phenotype (Kharkovets T, et al. EMBO J 2006; 25(3): 642-52. Epub 2006 Jan. 26). The heterozygous Kcnq4$^{+/dn}$ mutant mouse carries the equivalent mutation (G286S) to the human G285S mutation and shows progressive deafness.

siRNAs: siRNAs directed at the G286S, G286C, L275H and W277S alleles of Kcnq4 are identified and synthesized using methods described in Example 1 above. Target sequences of murine Kcnq4 are selected according to their GC content, and their specificity is tested using the BLAST search engine to exclude siRNAs with matches of >13 nucleotides to other mouse mRNAs or expressed sequence tags. For the G286S allele, siRNAs are identified to the following target sequences:

```
wild type sequence
                                        (SEQ ID NO:84)
5'-CGATTACATT GACAACCATC GGCTATGGTG ACAAGACACC
G-3'

G286S allele sequence
                                        (SEQ ID NO:85)
5'-CGATTACATT GACAACCATC AGCTATGGTG ACAAGACACC
G-3'
``` siRNAs that have the same nucleotide composition but are scrambles of identified siRNAs are generated and used as controls (on the World Wide Web at genscript.com/ssl-bin/app/scramble, GenScript Corp). Sense and antisense siRNAs are chemically synthesized and PAGE purified with 2'-deoxythymidine residues as 2 nucleotide overhangs at the 3' end of 19 nucleotide RNA duplexes.

Design of siRNAs to Kcnq4 allele variants. siRNAs are identified to selectively silence expression of allele variants of Kcnq4. Approximately 5 siRNA constructs are made for each mutant. To target the missense mutations, 22 nucleotide long (22-mer) siRNAs are designed with the mutated nucleotide in positions 9, 10, 11 or 12. siRNAs are designed in this fashion because it has been shown in embryo lysate that synthetic 21 and 22 nucleotide RNA duplexes are able to induce sequence-specific degradation of mRNA in the presence of ribonuclease III enzyme (dicer) (Elbashir S M, et al. EMBO J 2001; 20(23): 6877-88). The single-stranded target RNA is cleaved in the middle of the region complementary to the siRNA (Elbashir S M, et al. EMBO J 2001; 20(23): 6877-88).

In vitro silencing of mutant Kcnq4 expression. The ability of identified siRNAs to selectively suppress expression of the mutant Kcnq4 and not wild type Kcnq4 is assayed in mammalian cell lines by testing approximately 5 siRNA constructs for each mutant to identify the construct that most effectively meets these conditions. For the G286S mutation, CMV-driven mammalian expression vectors conferring murine Kcnq4$_{G286S}$-[eGFP] and Kcnq4$_{Wild\ type}$ [eYFP or eRFP]) are constructed and introduced into a mouse cell line that does not endogenously express Kcnq4. The suppression potency of each siRNA is determined and quantitated by fluorescence microscopy. Specificity will be measured by comparing results to expression levels observed with negative control siRNAs.

In vivo silencing of the Kcnq4 G286S allele by RNA interference. The most potent and specific siRNA is used to determine the in vivo efficacy of RNA interference in preventing progression of hearing loss in the Kcnq4$^{+/dn}$ mutant mouse (kindly provided in collaboration with Professor Thomas Jentsch at the University of Hamburg). The selected siRNAs are complexed with cationic liposome and delivered to the mouse cochlea using methodology the inventors have previously established (Jero J, et al. Hum Gene Ther 2001; 12(5): 539-48). In brief, the round window membrane (RWM) of the cochlea is exposed using an atraumatic anterior cervical approach to the middle ear. Gelfoam® absorbable gelatin sponge containing 1-5 µl of siRNA-liposome complex is placed against the RWM to facilitate delivery into the cochlea. Two study groups are investigated to assess RNAi in vivo: (1) 25 µg negative control siRNAs and (2) 25 µg KCNQ4-targeting siRNAs. The effect of the siRNAs is measured by RT-PCR analysis of Kcnq4 expression in microdissected cochlear tissue at 48, 72 and 120 hours post-treatment. Phenotypic effects of the siRNA treatment is quantified by recording of auditory brainstem responses (ABRs) to click stimuli between 0-100 decibels (db) sound pressure level (SPL) post-treatment at the same time intervals. Hearing test results are compared to the contralateral (non-operated) ear and to measurements in untreated mice.

The preservation of auditory function is central to the treatment of individuals with severe hereditary hearing impairment. For such individuals preventative or restorative therapies are currently unavailable and only synthetic hearing aids and cochlear implants provide artificial improvement, albeit sub-optimal. The studies described here confirm that post-transcriptional silencing using RNAi provides protection against hearing loss.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. All referenced publications, patents and patent documents are intended to be incorporated by reference, as though individually incorporated by reference.

What is claimed is:

1. A composition comprising an isolated RNA molecule comprising a first portion, wherein the first portion is no more than 30 nucleotides in length, wherein the first portion comprises a sequence that is complementary to target sequence 5'-AAC GTG TGC TAC GAT CAC TAC-3' (siRNA1; SEQ ID NO:1).

2. The composition of claim 1, further comprising a second portion, wherein the second portion has a sequence that is complementary to the first portion.

3. The composition of claim 2, wherein the first portion is operably linked to the second portion via a linker molecule.

4. The composition of claim 3, wherein the linker molecule is a polynucleotide linker.

5. The composition of claim 3, wherein the linker molecule is a non-nucleotide linker.

6. The composition of claim 5, wherein the linker molecule forms a loop of a hairpin.

7. The composition of claim 6, wherein the linker molecule is about 4 to about 10 nucleotides in length.

8. The composition of claim 1, wherein the first portion is from about 19 to about 23 nucleotides in length.

9. The composition of claim 1, wherein the first portion comprises about 21 nucleotides.

10. The composition of claim 2, wherein about 19 nucleotides of the first portion is base-paired to the complementary nucleotides of the second portion and wherein at least two 3' terminal nucleotides of first and second portions are not base-paired to the nucleotides of the other portion.

11. The composition of claim 9, further comprising a second portion, wherein all of the about 21 nucleotides of the first portion are base-paired to the complementary nucleotides of the second portion.

12. A vector comprising a nucleic acid molecule encoding the composition of claim 1.

13. A host cell comprising the vector of claim 12.

14. A pharmaceutical composition comprising the composition of claim 1 or the vector of claim 12.

15. The pharmaceutical composition of claim 14, further comprising a liposome.

16. The pharmaceutical composition of claim 14, further comprising a pharmaceutically acceptable carrier or diluent.

\* \* \* \* \*

```
                        SEQUENCE LISTING

<160> NUMBER OF SEQ ID NOS: 95

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aacgtgtgct acgatcacta c                                                 21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aatgtatgct acgaccacca c                                                 21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aagttcatca aggggagat a                                                  21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aagttcatga agggagagat a                                                 21

<210> SEQ ID NO 5
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 5
aagactgtct tcacagtgtt c                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaggaggtgt ggggagatga g                                              21

<210> SEQ ID NO 7
<211> LENGTH: 731
<212> TYPE: DNA
<213> ORGANISM: Homo sapiens

<400> SEQUENCE: 7
ggccccgccg cgcttcctcc cgacgcagag caaaccgccc agagtagaag atggattggg     60
gcacgctgca gacgatcctg ggggtgtga acaaacactc caccagcatt ggaaagatct    120
ggctcaccgt cctcttcatt tttcgcatta tgatcctcgt tgtggctgca aaggaggtgt   180
ggggagatga gcaggccgac tttgtctgca acaccctgca gccaggctgc aagaacgtgt   240
gctacgatca ctacttcccc atctcccaca tccggctatg ggccctgcag ctgatcttcg   300
tgtccacgcc agcgctccta gtggccatgc acgtggccta ccggagacat gagaagaaga   360
ggaagttcat caaggggag ataaagagtg aatttaagga catcgaggag atcaaaaccc    420
agaaggtccg catcgaaggc tccctgtggt ggacctacac aagcagcatc ttcttccggg   480
tcatcttcga agccgccttc atgtacgtct ctatgtcat gtacgacggc ttctccatgc    540
agcggctggt gaagtgcaac gcctggcctt gtcccaacac tgtggactgc tttgtgtccc   600 ggccccacgga gaagactgtc ttcacagtgt tcatgattgc agtgtctgga atttgcatcc   660
tgctgaatgt cactgaattg tgttatttgc taattagata ttgttctggg aagtcaaaaa   720
agccagttta a                                                        731

<210> SEQ ID NO 8
<211> LENGTH: 729
<212> TYPE: DNA
<213> ORGANISM: Mus musculus

<400> SEQUENCE: 8
aacgctgcac gctcctccgg acacagtgcc aaccatccag aggacaagat ggattggggc     60
acactccaga gcatcctcgg gggtgtcaac aaacactcca ccagcattgg aaagatctgg    120
ctcacggtcc tcttcatctt ccgcatcatg atcctcgtgg tggctgcaaa ggaggtgtgg    180
ggagatgagc aagccgattt tgtctgcaac acgctccagc ctggctgcaa gaatgtatgc    240
tacgaccacc acttccccat ctctcacatc cggctctggg ctctgcagct gatcatggtg    300
tccacgccag ccctcctggt agctatgcat gtggcctacc ggagacatga aagaaacgg     360 aagttcatga aggagagat aaagaacgag tttaaggaca cgaagagat caaacccag       420 aaggtccgta tcgaagggtc cctgtggtgg acctacacca ccagcatctt cttccgggtc    480
```

```
atctttgaag ccgtcttcat gtacgtcttt tacatcatgt acaatggctt cttcatgcaa    540
cgtctggtga aatgcaacgc ttggccctgc cccaatacag tggactgctt catttccagg    600
cccacagaaa agactgtctt caccgtgttt atgatttctg tgtctggaat ttgcattctg    660
ctaaatatca cagagctgtg ctatttgttc gttaggtatt gctcaggaaa gtccaaaaga    720
ccagtctaa                                                             729
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caaccatcag ctatggtgac a                                                21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
acaaccatca gctatggtga c                                                21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gacaaccatc agctatggtg a                                                21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gctctggtcg gggacgatta c                                                21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgctctggtc ggggacgatt a                                                21

<210> SEQ ID NO 14
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
acgctctggt cggggacgat t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
taggctccag ctttgccctg a                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctaggctcca gctttgccct g                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cctaggctcc agctttgccc t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
caaccatctg ctatggtgac a                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
acaaccatct gctatggtga c                                              21

<210> SEQ ID NO 20
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 20
gacaaccatc tgctatggtg a                                             21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcctgcggcc cgcgcacaag c                                             21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgcctgcggc ccgcgcacaa g                                             21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ccgcctgcgg cccgcgcaca a                                             21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gattacatcg acaaccatcg g                                             21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cgattacatc gacaaccatc g                                             21

<210> SEQ ID NO 26
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 26
acgattacat cgacaaccat c                                                    21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cgactcgcac tggtggggga c                                                    21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ccgactcgca ctggtggggg a                                                    21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gccgactcgc actggtgggg g                                                    21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tcgcattacg atcctcgttg t                                                    21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ttcgcattac gatcctcgtt g                                                    21

<210> SEQ ID NO 32
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 32
tttcgcatta cgatcctcgt t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cccacatctg gctatgggcc c                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcccacatct ggctatgggc c                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ctcccacatc tggctatggg c                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tgtgctacca tcactacttc c                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gtgtgctacc atcactactt c                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 38
cgtgtgctac catcactact t                                               21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcagccagcc tgcaagaacg t                                               21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tgcagccagc ctgcaagaac g                                               21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctgcagccag cctgcaagaa c                                               21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cttcttccag gtcatcttcg a                                               21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tcttcttcca ggtcatcttc g                                               21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 44
atcttcttcc aggtcatctt c                                                     21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tggaattttc atcctgctga a                                                     21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ctggaatttt catcctgctg a                                                     21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tctggaattt tcatcctgct g                                                     21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gaggtgtgcg gagatgagca g                                                     21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggaggtgtgc ggagatgagc a                                                     21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 50
aggaggtgtg cggagatgag c                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agcaggccaa ctttgtctgc a                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gagcaggcca actttgtctg c                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tgagcaggcc aactttgtct g                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tcctggggcg tgtgaacaaa c                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
atcctggggc gtgtgaacaa a                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
```

```
gatcctgggg cgtgtgaaca a                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
caaacacttc accagcattg g                                              21

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
caaacacttc accagcattg                                                20

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
caaacacttc accagcatt                                                 19

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ccacatccag ctatgggccc t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cccacatcca gctatgggcc c                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
```
tcccacatcc agctatgggc c                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
agcaggccta ctttgtctgc a                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gagcaggcct actttgtctg c                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tgagcaggcc tactttgtct g                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
acactgtgaa ctgctttgtg t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
aacactgtga actgctttgt g                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
caacactgtg aactgctttg t                                              21

```
<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ggaggtgtcg ggagatgagc a                                                  21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aggaggtgtc gggagatgag c                                                  21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
aaggaggtgt cgggagatga g                                                  21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ttgggggatg ctgcacactt t                                                  21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
attgggggat gctgcacact t                                                  21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gattggggga tgctgcacac t                                                  21
```

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gaaccagtga aatgccagat a                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ggaaccagtg aaatgccaga t                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tggaaccagt gaaatgccag a                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gaaccagtga aatgccagat a                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ggaaccagtg aaatgccaga t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tggaaccagt gaaatgccag a                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
gaaccagtga aatgccagat a             21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 82
ggaaccagtg aaatgccaga t             21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
tggaaccagt gaaatgccag a             21

<210> SEQ ID NO 84
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84
cgattacatt gacaaccatc ggctatggtg acaagacacc g             41

<210> SEQ ID NO 85
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
cgattacatt gacaaccatc agctatggtg acaagacacc g             41

<210> SEQ ID NO 86
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86 ttcagaagg             9

<210> SEQ ID NO 87

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aagactgtct tcaccgtgtt t                                             21

<210> SEQ ID NO 88
<211> LENGTH: 19
<212> TYPE: DNA
<213> ORGANISM: Homo sapiens

<400> SEQUENCE: 88
ttcctcccga cgcagagca                                                19

<210> SEQ ID NO 89
<211> LENGTH: 19
<212> TYPE: DNA
<213> ORGANISM: Homo sapiens

<400> SEQUENCE: 89
gactttgtct gcaacaccc                                                19

<210> SEQ ID NO 90
<211> LENGTH: 20
<212> TYPE: DNA
<213> ORGANISM: Mus musculus

<400> SEQUENCE: 90
tcctccggac acagtgccaa                                               20

<210> SEQ ID NO 91
<211> LENGTH: 21
<212> TYPE: DNA
<213> ORGANISM: Mus musculus

<400> SEQUENCE: 91
agaaggtccg tatcgaaggg t                                             21

<210> SEQ ID NO 92
<211> LENGTH: 20
<212> TYPE: DNA
<213> ORGANISM: Homo sapiens

<400> SEQUENCE: 92
actttgtctg caacaccctg                                               20

<210> SEQ ID NO 93
<211> LENGTH: 20
<212> TYPE: DNA
<213> ORGANISM: Homo sapiens

<400> SEQUENCE: 93
ggagatcaaa acccagaagg                                               20

<210> SEQ ID NO 94
<211> LENGTH: 20
<212> TYPE: DNA
<213> ORGANISM: Mus musculus

<400> SEQUENCE: 94
```

-continued

```
attttgtctg caacacgctc                                              20

<210> SEQ ID NO 95
<211> LENGTH: 20
<212> TYPE: DNA
<213> ORGANISM: Mus musculus

<400> SEQUENCE: 95
agagatcaaa acccagaagg                                              20
```